United States Patent [19]

Kiernan

[11] Patent Number: 4,522,822

[45] Date of Patent: Jun. 11, 1985

[54] PHENYLETHANE DERIVATIVES AND ACID ADDITION SALTS THEREOF FOR INCREASING LEAN MEAT DEPOSITION AND/OR IMPROVING LEAN MEAT TO FAT RATIO IN WARM BLOODED ANIMALS

[75] Inventor: Jane A. Kiernan, Kendall Park, N.J.

[73] Assignee: American Cyanamid Company, Stamford, Conn.

[21] Appl. No.: 530,848

[22] Filed: Sep. 9, 1983

Related U.S. Application Data

[60] Division of Ser. No. 219,055, Dec. 22, 1980, Pat. No. 4,407,819, which is a continuation-in-part of Ser. No. 181,255, Aug. 25, 1980, abandoned, which is a continuation-in-part of Ser. No. 143,070, Apr. 24, 1980, abandoned, which is a continuation-in-part of Ser. No. 66,909, Aug. 16, 1979, abandoned.

[51] Int. Cl.$^3$ ............................................. A61K 31/42
[52] U.S. Cl. .................................................. 514/376
[58] Field of Search ........................................ 424/272

[56] References Cited

U.S. PATENT DOCUMENTS

| | | | |
|---|---|---|---|
| 3,348,999 | 10/1967 | Woroch et al. | 424/272 |
| 3,754,000 | 8/1973 | Fauran et al. | 424/272 |
| 4,179,442 | 12/1979 | Köllensperger et al. | 424/272 |
| 4,186,129 | 1/1980 | Huth et al. | 424/272 |
| 4,188,323 | 2/1980 | Pestellini et al. | 424/272 |

FOREIGN PATENT DOCUMENTS 2935902  2/1981  Fed. Rep. of Germany ...... 424/272

*Primary Examiner*—Douglas W. Robinson
*Attorney, Agent, or Firm*—Estelle J. Tsevdos; H. G. Jackson

[57] ABSTRACT

There is provided a method for increasing lean meat deposition and/or improving lean meat to fat ratio in poultry, domestic pets, sheep, swine, rabbits, goats and cattle by administering, orally or parenterally, to said animals an effective amount of a phenylethane derivative or acid salt thereof.

18 Claims, No Drawings

PHENYLETHANE DERIVATIVES AND ACID ADDITION SALTS THEREOF FOR INCREASING LEAN MEAT DEPOSITION AND/OR IMPROVING LEAN MEAT TO FAT RATIO IN WARM BLOODED ANIMALS

This application is a divisional of co-pending parent application Ser. No. 219,055, filed Dec. 22, 1980, now issued as U.S. Pat. No. 4,407,819, on Oct. 4, 1983.

The parent application is a continuation-in-part of co-pending application Ser. No. 181,255 filed Aug. 25, 1980 (abandoned) which is a continuation-in-part of Ser. No. 143,070 filed Apr. 24, 1980 (abandoned) which in turn is a continuation-in-part of Ser. No. 66,909 filed Aug. 16, 1979 (abandoned).

SUMMARY OF THE INVENTION

Substitution products of certain 1-(aminodihalophenyl)-2-amino ethanes and the acid addition salts thereof are disclosed in U.S. Pat. No. 3,536,712, issued on Oct. 27, 1970. Specifically, patentees disclose methods for the synthesis of said compounds and state that said compounds are useful for enhancing the blood circulation, and as bronchodilators, analgesics, sedatives, antipyretics, antiphlogistics and antitussives in warm-blooded animals.

Other related 1-aminodihalophenyl)-2 aminoethanols and their derivates are disclosed in Japanese Kokai No. 77 83,619 (Chemical Abstracts, 87, 201061r), German Offenlegungsschrift No. 2,804,625 (1979), German Offenlegungsschrift No. 2,157,040 (1973), German Offenlegungsschrift No. 2,261,914 (1974), European Patent Application No. 8,715 (1980), Netherlands Patent Application No. 7,303,612 (1973). These applications disclose uses selected from analgesics, broncholytic, anti-inflammatory, uterine spasmolytic, $\beta$-mimetic and/or $\beta$-blocking activities, antispasmolytic activity on cross-striped muscle structure, for tocology, reducing blood pressure by peripheral vasodilation and mobilizing body fat, and for treating allergies.

The patentees and authors referred to above do not, however, indicate or suggest that said compounds are useful for increasing lean meat deposition and/or improving the lean meat to fat ratio in warm-blooded animals, particularly farm and domestic animals, such as swine, poultry, dogs, sheep, goats, rabbits, cats and cattle. The term lean meat is used hereafter interchangeably with the amount of muscle or protein measured.

It is, therefore, surprising to find that a compound having a formula selected from the group consisting of:

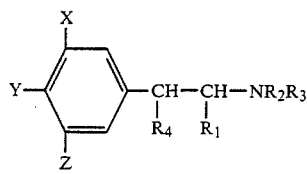
(I)

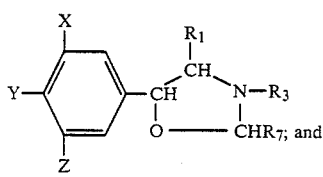
(Ia)

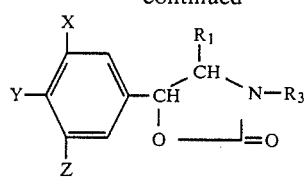
(Ib)

wherein

X is hydrogen, halogen, or —CN;
Y is hydrogen, $NR_8R_9$ or $NHCOR_5$:
Z is halogen, OH, $CF_3$, —CN, COOR, $CONH_2$, $C_1$–$C_4$ alkyl alkoxy nitro, or $C_1$–$C_4$ dialkylaminomethyl;
$R_1$ is hydrogen or $C_1$–$C_4$ alkyl;
$R_2$ is hydrogen, methyl, ethyl; $C_2$–$C_5$ alkanoyl, or

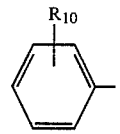

$R_3$ is $C_1$–$C_5$ alkyl, $C_3$–$C_4$ alkenyl, $C_3$–$C_5$ cycloalkyl; 2-hydroxyethyl, $\alpha,\alpha$-dimethylphenethyl, benzyl, 3-phenylpropyl or 3-(4-carbomethoxyphenyl) propyl;
$R_4$ is hydrogen, $OR_6$ or $SR_{11}$;
$R_5$ is hydrogen, $C_1$–$C_4$ alkyl, $C_1$–$C_4$ alkoxy,

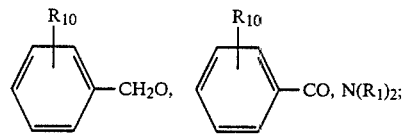

$R_6$ is hydrogen, $C_1$–$C_6$ alkyl, $C_2$–$C_5$ alkanoyl,

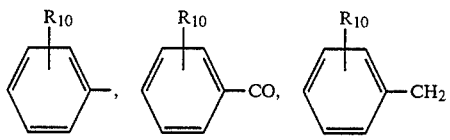

$R_7$ is hydrogen, $C_1$–$C_4$ alkyl or phenyl;
$R_8$ is hydrogen, $C_1$–$C_4$ alkyl or $C_3$–$C_4$ alkenyl
$R_9$ is hydrogen, $C_1$–$C_6$ alkyl, $C_4$–$C_6$ cycloalkyl, $C_3$–$C_4$ alkenyl, benzyl;
$R_{10}$ is chloro, dichloro, methyl, dimethyl, methoxy, dimethoxy or nitro;
$R_{11}$ is $C_1$–$C_6$ alkyl, phenyl, benzyl; and when $R_8$ and $R_9$ are taken together with the nitrogen to which they are attached, they may represent pyrrolidino; with the provisos that when $R_3$ is $\alpha,\alpha$-dimethylphenethyl, $C_3$–$C_6$ cycloalkyl, benzyl, 3-phenylpropyl or 3-(4-carbomethoxyphenyl) propyl, $R_2$ is hydrogen, $C_2$–$C_5$ alkanoyl or benzoyl; and when $R_3$ is hydroxyethyl, $R_2$ and $R_6$ are hydrogen and the compound is (I); and when $R_6$ is $C_2$–$C_5$ alkanoyl or

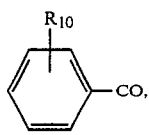

$R_2$ and $R_3$ are substituents other than hydrogen, except when $R_3$ is an alkyl or substituted alkyl group which contains a tertiary carbon attached to nitrogen; and when Y is hydrogen, X and Z are halogen, $R_2$ is hydrogen, $C_2$-$C_5$ alkanoyl or

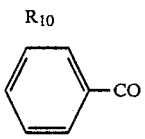

and $R_3$ is isopropyl, 2-butyl or tert-butyl; and when Z is OH, X and Y are hydrogen; and when X is —CN, Z is —CN; and when $R_5$ is $N(R_1)_2$, $R_6$ is hydrogen; when $R_8$ is $C_1$-$C_4$ alkyl or $C_3$-$C_4$ alkenyl, $R_9$ is $C_1$-$C_4$ alkyl or $C_3$-$C_4$ alkenyl; racemic mixtures of the above-identified compounds and the optically active isomers, and non-toxic, pharmacologically acceptable acid addition salts thereof, when administered to swine, poultry, such as chickens and turkeys, cattle, sheep, goats or domestic pets, increases the lean meat deposition on said animals, improves the lean meat to fat ratio thereof and enhances the dressed carcass weight of said animals. Moreover, in the treatment of swine it is particularly effective to administer the compounds of the invention to pigs being prepared for market and weighing between 30 kg and market weight which could be in excess of 125 or 150 kg.

A preferred group of compounds of formula I for use in the method of this invention have the above structure wherein X is hydrogen or halogen; Y is hydrogen, $NR_8R_9$ or NH—$COR_5$; Z is halogen, OH, CN or $CF_3$; $R_1$ is hydrogen or $C_1$-$C_4$ alkyl; racemic mixtures of the above-identified compounds and the optically active isomers and non-toxic, pharmacologically acceptable acid addition salt thereof.

Another preferred group of compounds of formula I for use in the method of this invention have the above structure wherein X is hydrogen, chlorine and bromine; Y is hydrogen or $NR_8R_9$; Z is chlorine, bromine, CN or $CF_3$; R is hydrogen; $R_4$ is H, $OR_6$ wherein $R_6$ is hydrogen, $C_1$-$C_6$ alkyl, $C_1$-$C_6$ alkanolyl or benzoyl; racemic mixtures of the above-identified compounds and the optically active isomers and non-toxic, pharmacologically acceptable acid addition salt thereof.

It is found that, in addition to the methods of preparation disclosed in the cited art, the formula (I) compounds (wherein Y is hydrogen) may also be prepared by the condensation of an appropriately substituted styrene presence of an inert solvent, such as a lower alcohol at or near the boiling point of same, as shown below:

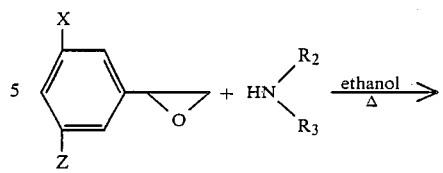

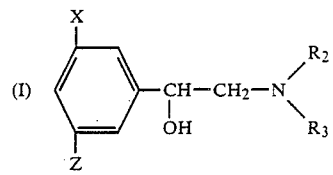

wherein X and Z are halogen, $R_2$ and $R_3$ are as hereinabove defined and Y is hydrogen. Thus, for instance, one mole of 3,5-dichlorostyrene oxide can be reacted with an equimolar or excess amount of t-butylamine in ethanol at reflux from about 1 to about 8 hours, or until the reaction is essentially complete and the desired α-[(t-butylamino)methyl]-3,5-dichlorobenzyl alcohol is obtained.

The styrene oxide intermediate can be prepared by reducing the corresponding phenacyl bromide with $NaBH_4$ at 5° C. or lower in the presence of an anhydrous lower alcohol, such as ethanol. The phenacyl bromide intermediate in turn is prepared by brominating the appropriately substituted acetophenone with cupric bromide in the presence of chloroform and ethyl acetate. The above sequence may be graphically illustrated as follows:

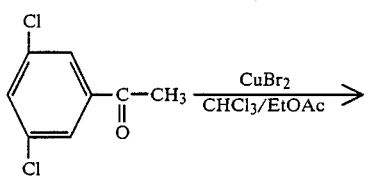

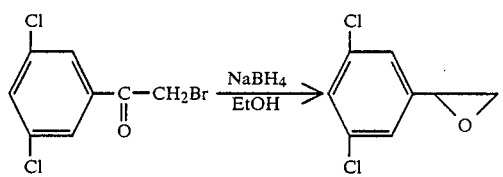

Alternatively, formula (I) compounds above wherein Y is hydrogen may be prepared from the corresponding formula (I) compound wherein Y is amino, via a deamination reaction, as follows:

The amine is dissolved in 50–52% aqueous hypophosphorous acid ($H_3PO_2$), the solution is chilled below 10° C., and an equimolar or excess amount of sodium nitrite is added as an aqueous solution with stirring over a period of time. On completion of the addition, the reaction mixture is warmed to room temperature and stirred for an additional period of time. The product is then recovered from the reaction mixture by standard laboratory procedures and purified if so desired.

The preparation of 4-substituted aminoacetophenones required for the preparation of 4-substituted phenylethanolamines by conventional means, which are now found to be useful for raising meat-producing animals, is exemplified as follows:

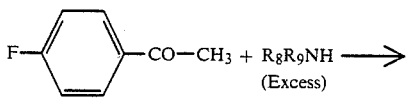

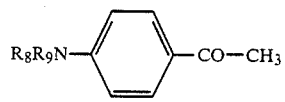

The fluorine displacement is carried out with excess amine in the presence of a solvent and if a solvent is required, water appears to be the most useful. With volatile amines, the reaction is conducted in a sealed vessel and generally temperatures of 50°–100° C. are sufficient to complete the reaction.

Chlorination and bromination of these aminoacetophenones may be conducted with N-chlorosuccinimide and N-bromosuccinimide in toluene, chlorobenzene or dichlorobenzene at 90°–100° C. Iodination may be conducted with NaI/N,N-dichlorobenzenesulfonamide or iodine monochloride in acetic acid.

By reacting these acetophenones with bromine in chloroform or methylene chloride, the corresponding phenacyl bromides are prepared. These phenacyl bromides are then reacted with $R_2R_3N$ amines and the aminoketones are reduced with $NaBH_4$ or $NaCNBH_3$ by conventional techniques described in references cited hereinbefore.

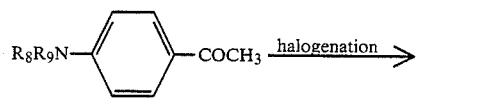

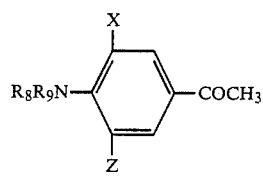

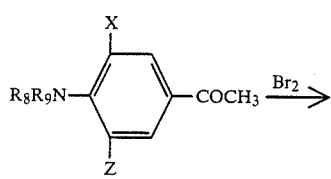

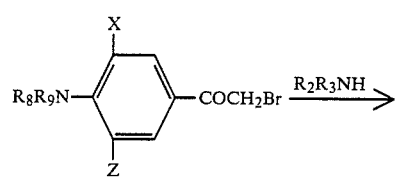

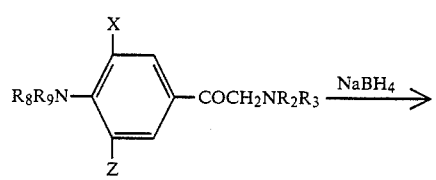

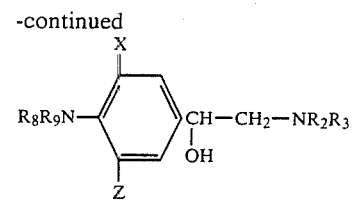

wherein X and Z are hydrogen; chlorine, bromine or iodine and $R_2$ and $R_3$ are hydrogen; $C_1$–$C_4$ alkyl, or $C_2$–$C_3$ alkenyl groups.

The compounds of formula I, wherein $R_8$ and $R_9$ are groups other than both being hydrogen are also prepared by the following general scheme:

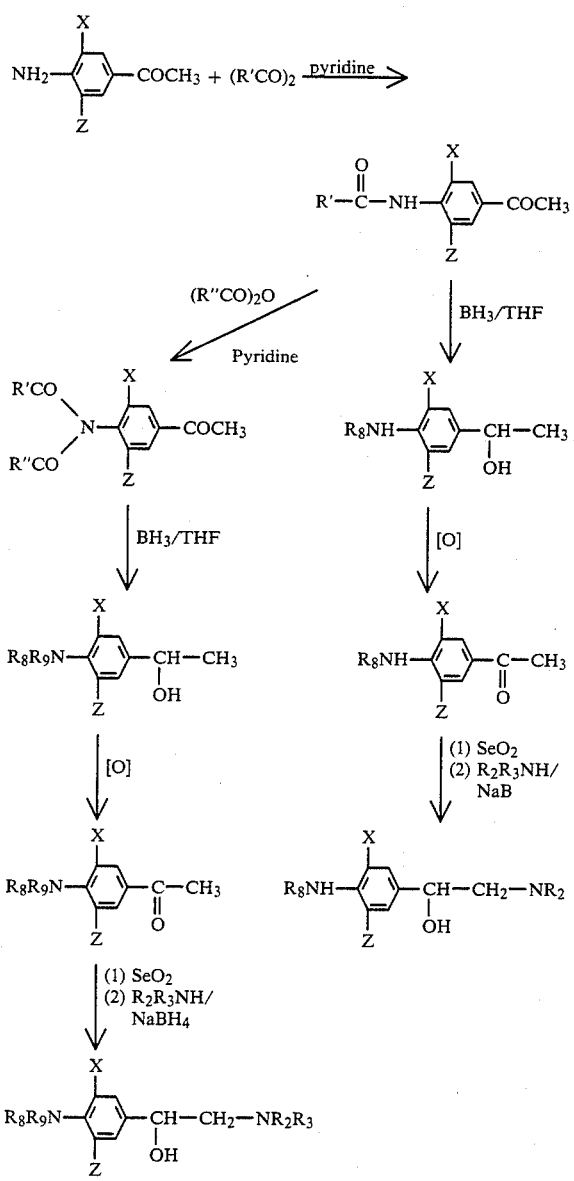

The methods utilized in the above scheme are either reported in references cited hereinbefore or by conventional methods. Oxidation of the alcohol may be conducted with chromic acid (Jones Reagent), $MnO_2$, pyridinium chlorochromate, or other oxidizing agents. Where X or Z are the $BH_3$-reducible groups CN, COOR, or CONH$_2$, the appropriate acetophenones are prepared by displacement of X or Z represented by bromine with CuCN/DMF at 100°–150° C. by the conventional method after reduction of the acylated aminoacetophenones in the first step followed by re-oxidation in the second step of the above procedure. The cyano substituted-aminoacetophenones are then converted to their corresponding ethanolamines, which are then converted to the desired esters, acids and amides by conventional methods, such as R$_1$OH/acid→esters, hydrolyses→acids and partial hydrolyses→amides.

Furthermore, compounds of the following structure are prepared by allowing the corresponding ethanolamines to react with an equivalent or slight excess of the acid anhydrides with or without organic bases, such as tertiary amines or pyridine. The reactions are conducted in inert solvents

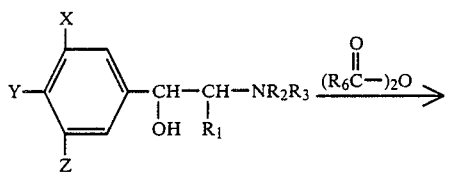

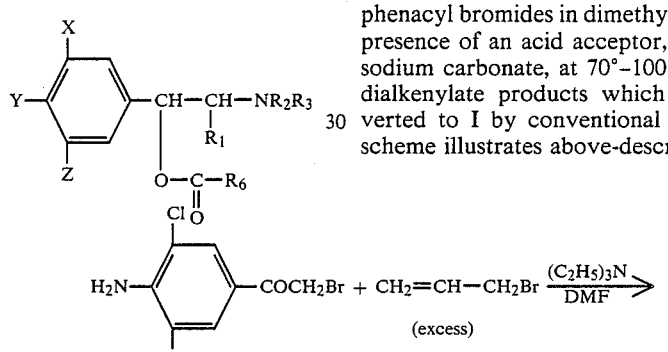

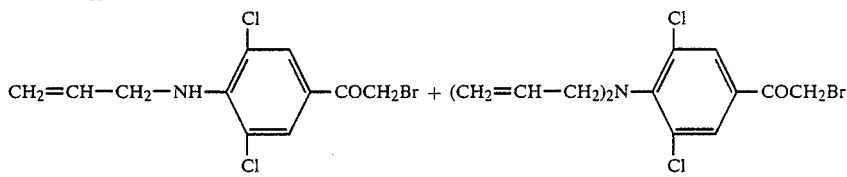

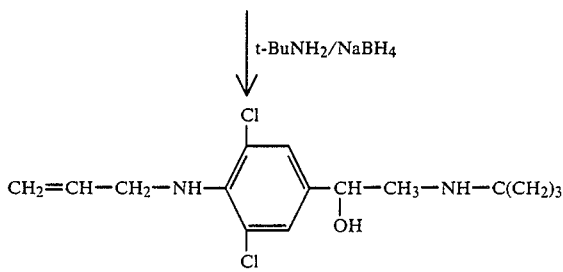

such as chlorinated hydrocarbons, aromatic solvents at 0°–25° C. Reaction of the anhydride at the hydroxyl group proceeds well provided R$_2$ and R$_3$ are groups other than hydrogen and when R$_2$ is hydrogen, R$_3$ is a substituent containing a tertiary carbon attached to nitrogen.

Compounds of the following structure which contain alkanoyl or aroyl groups on the ethanolamine moiety are readily prepared by using 2 equivalents or more of the acid anhydrides in the presence of a tertiary amine, such as triethylamine, or pyridine in an inert solvent (CH$_2$Cl$_2$, CHCl$_3$, toluene, etc.) at 50°–100° C.

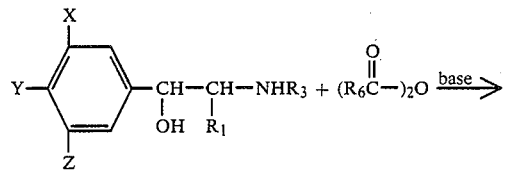

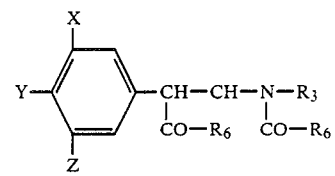

Additionally, Formula I compounds, wherein R$_8$ and R$_9$ are selected from hydrogen and C$_3$–C$_4$ alkenyl, are prepared by alkenylation of 4-amino-3,5-disubstituted phenacyl bromides in dimethylformamide (DMF) in the presence of an acid acceptor, such as triethylamine or sodium carbonate, at 70°–100° C. to afford mono- and dialkenylate products which are separated and converted to I by conventional methods. The following scheme illustrates above-described general method:

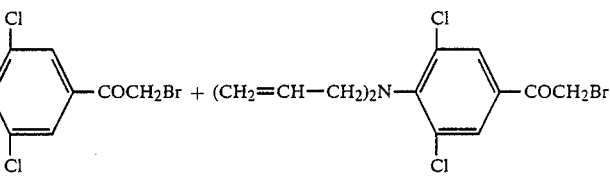

Formula (I) compounds wherein R$_4$ is OR$_6$ and SR$_{11}$, wherein R$_6$ and R$_{11}$ are as hereinabove defined, may be prepared by converting the alcohol (R$_4$=OH) with thionyl chloride under an inert blanket of gas such as nitrogen at a temperature range of from about 0° C. to 10° C., and preferably at 0° to 5° C. for a reaction period sufficient to essentially complete the reaction. The thus obtained halo compound is isolated by conventional methods and is then reacted with the appropriate alcohol or mercaptan, under an inert blanket of gas, such as nitrogen at a temperature range of from about 0° to 50° C. The formula (I) product thus obtained is then isolated by standard laboratory methods and purified, if so desired. The above reaction sequence may be graphically illustrated as follows:

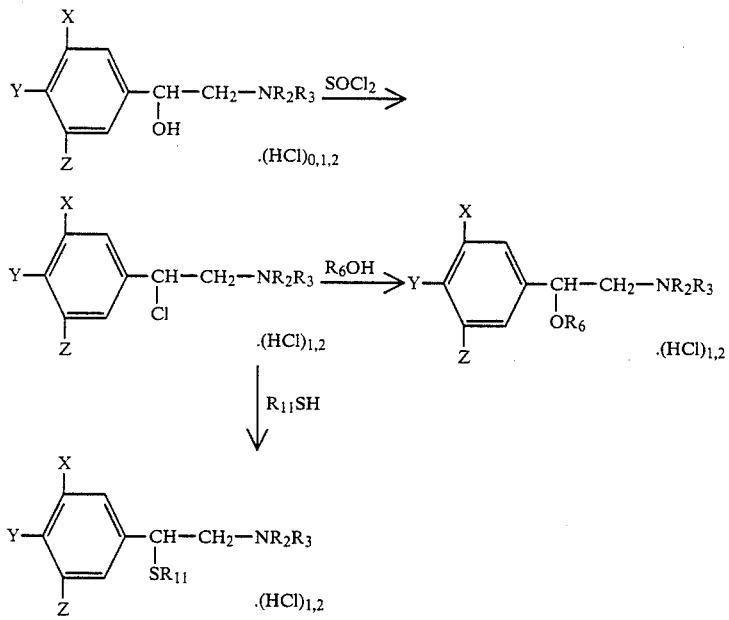

wherein X, Y, Z, $R_2$, $R_6$, and $R_{11}$ are as hereinabove defined.

These displacement reactions may also be performed by using an excess of alkoxide ($R_6O^-$) or mercaptide ($R_{11}S^-$) in an inert solvent such as tetradrofuran to afford the above ethers and thioethers in a similar manner.

Alternatively, a formula (I) compound wherein $R_4$ is $OR_6$ may be prepared by dissolving the corresponding $R_6OH$ alcohol and saturating the thus obtained solution with dry HCl gas. The reaction mixture is then stirred at room temperature for a period of time sufficient to essentially complete the reaction and the product is then isolated by standard laboratory procedures and purified if so desired. This reaction sequence may be illustrated as follows:

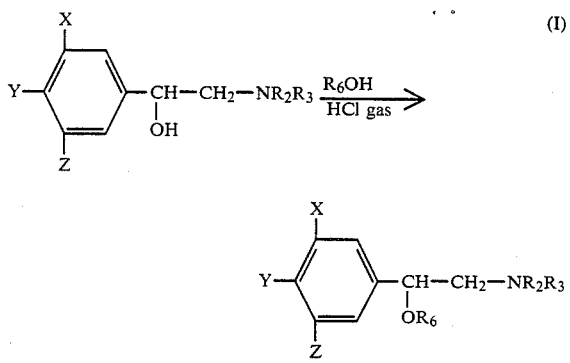

wherein X, Y, Z, $R_2$, $R_3$ and $R_6$ are as hereinabove defined.

Among the acid addition salts which can be prepared and used in accordance with the present invention are the hydrochloric acid, phosphoric acid, acetic acid, citric acid, gluconic acid and propionic acid addition salts. In accordance with the process of the invention, it has been found that the increase in lean meat deposition and improvement in lean meat to fat ratio in swine, poultry, sheep, goats, cattle, and domestic pets can be achieved by administering to said animals can effective amount of a formula I phenylethanolamine, or the acid addition salt thereof, in the animal feed. The phenylethane, or acid addition salt, may also be administered in the form of an animal feed concentrate as a top dressing for the animals daily ration or it may be administered as a subcutaneous implant in the form of paste or pellets.

Animal feed compositions effective for increasing lean meat deposition and for improving lean meat to fat ratio in poultry, swine, sheep, goats, domestic pets and cattle are generally prepared by admixing a formula (I) phenylethane derivative or acid addition salt thereof or an animal feed supplement containing said compound with a sufficient amount of animal feed to provide from about 1 to 1000 ppm of said compound in the feed.

Animal feed supplements can be prepared by admixing about 75% to 95% by weight of a formula I phenylethane derivative or acid addition salt thereof with about 5% to 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed.

If the supplement is used as a top dressing for feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed.

The preferred poultry and domestic pet feeds usually contain about 0.01 to 400 grams and preferably 10 to 400 grams of active ingredient per ton of feed.

For parenteral administration the pehnylethane derivative may be prepared in the form of a paste or pellet and administered as an implant, usually under the skin of the head or ear of the animal in which increase in lean meat deposition and improvement in lean meat to fat ratio is sought.

In general parenteral administration involves injection of a sufficient amount of the above-said phenylethane derivative to provide the animal with 0.001 to 100 mg/kg/day of body weight of the active ingredient. The preferred dosage for swine, cattle, sheep and goats is in the range of from 0.001-to 50 mg/kg/day of body weight of the active phenylethane derivative; whereas, the preferred dose level of said phenylethane derivative for poultry and domestic pets is usually in the range of from 0.001 to 35 mg/kg/day of body weight.

Paste formulations can be prepared by dispersing the active phenylethane derivative in a pharmaceutically acceptable oil such as peanut oil, sesame oil, corn oil or the like.

Pellets containing an effective level of the phenylethane derivative can be prepared by admixing the above-said active ingredient with a diluent such as carbowax, carnuba wax, or the like, and a lubricant, such as magnesium or calcium stearate, can be added to improve the pelleting process.

It is, of course, recognized that more than one pellet may be administered to an animal to achieve the desired dose level which will provide the increase in lean meat desposition and improvement in lean meat to fat ratio desired. Moreover, it has been found that implants may also be made periodically during the animal treatment period in order to maintain the proper drug level in the animal's body.

The method of the present invention has several advantages; for the pet owner or veterinarian who wishes to increase leaness and trim unwanted fat from pet animals, the present invention provides the means by which this can be accomplished. For the poultry mean and swine raisers, using the method of the present invention yields leaner animals which command higher prices from the meat industry. Surprisingly, it is also noted that feed efficiency and/or animal growth rate are significantly enhanced when the compounds of the present invention are administered to swine and poultry at selected dose levels.

These and other advantages will become apparent from the examples set forth below. Such examples are provided only for exemplification of the invention and are not to be considered as limiting the invention.

EXAMPLE 1

Evaluation of test compounds as antilipogenic agents—Mouse tests

CFI female mice from Carworth Farms are received when they are six weeks old. They are housed ten to a cage in air-conditioning rooms (22° C. to 25° C.) with automatically controlled lights, 14 hours on and 10 hours off. The basal diet used in these studies is Purina Laboratory Chow (see description below), which is supplied ad libitum.

The following is a description of the diet to which the growth-promoting compounds were added.

| DIET Guaranteed Analysis | |
| --- | --- |
| Crude protein not less than | 23.0% |
| Crude fat not less than | 4.5% |
| Crude fiber not more than | 6.0% |
| Ash not more than | 9.0% |

Ingredients

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide. Water is also allowed ad libitum.

Thirteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Table I below wherein data are reported as percent body fat, percent change in body fat from controls and gain per mouse in grams.

TABLE I

Antilipogenic Agent Evaluation and Growth Enhancement Evaluation in Mice

| Compound | Level in Diet (ppm) | Number of Mice per Treatment | Average Initial Weight (g) | Average Final Weight (g) | Gain per Mouse (g) | Percent Body Fat | Change in Fat from Control |
| --- | --- | --- | --- | --- | --- | --- | --- |
| 2,6-dichloro-4-amino-α-[(tert-butylamino)methyl]benzyl alcohol hydrochloride (H₂N-C₆H₂Cl₂-CH(OH)-CH₂-NH-C(CH₃)₃·HCl) | 0 | 50 | 23.6 | 25.0 | 1.4 | 11.95 | — |
| | 50 | 30 | 23.7 | 26.0 | 2.3 | 11.95 | 0 |
| | 100 | 30 | 23.4 | 25.7 | 2.3 | 10.23 | −14.40 |
| | 200 | 30 | 23.5 | 25.3 | 1.8 | 10.50 | −12.13 |
| | 400 | 30 | 23.4 | 24.9 | 1.4 | 9.10 | −23.80 |

Percent Body Fat Determination of Mice

A. Preparation of Carcasses

Stomach and intestines are removed from each mouse. All other viscera, including skin and fur, remain intact. Each cage of mice (10) are weighed and added to a 1000 ml beaker and autoclaved at 120° C. (1.05 kg cm$^{-2}$ pressure) for 30 minutes. Carcasses from each cage are then blended and homogenized. The homogenate is weighed and duplicate 5-gram samples are removed for analysis.

B. Fat Analysis

Fifteen milliliters (ml) of concentrated hydrochloric acid is added to each 5-gram samples and mixed well. Samples are heated in an 84° C. water bath for 2 hours. To extract the fat, thirty ml of petroleum ether is added to each sample, 15 ml at a time, and mixed well on a Vortex mixer. The aqueous and organic phases are separated by low speed centrifugation and the ether layer (containing fat) is extracted into tared 30 ml beakers. After evaporating to dryness the beaker containing fat is reweighed to determine grams of fat per five grams of homogenate. Total body fat in the carcass is calculated as follows:

$$\% \text{ Fat} = \frac{\left[\begin{array}{c}\text{grams fat}\\\text{in sample}\end{array}\right]\left[\begin{array}{c}\text{grams total}\\\text{homogenate}\end{array}\right]}{\left[\begin{array}{c}\text{gram weight}\\\text{of sample}\end{array}\right]\left[\begin{array}{c}\text{carcass weight}\\\text{of mice (g)}\end{array}\right]} \times 100$$

EXAMPLE 2

Antilipogenic Evaluation of test compounds—Mouse Study

CFI female mice, 55 days old, are weighed in groups of 10 and allotted to cages to minimize weight variation among cages. Treatments are randomly assigned to cages.

Each of the treatments are tested in 3 replicates, i.e., in 3 cages of 10 mice each. There are 10 cages of 10 control mice each. Drugs are mixed in the diet at the dosage level indicated. Feed and water are offered ad libitum for 12-day test period. Feed spilled is collected during the test period. At the end of the test period, the collected feed is weighed and the mean feed consumption per cage of ten mice is determined for each treatment. The mice are weighed as a group of 10 and the weight gain determined. The mice are sacrificed by cervical dislocation. The right uterine fat pad of each mouse is removed. The fat pads for each cage of 10 mice are weighed as a unit.

To establish the correlation between the percent reduction in fat pad weights of treated animals and percent reduction in total body fat of treated animals, animals from several treatment groups are evaluated for total body fat using the body fat determination described in Example 1. Data obtained are reported in Table II for those groups upon which such determination had been made. From percent reduction in fat pad weight and the total fat determinations for the groups tested, it can be seen that a reduction in fat pad weights of animals is generally indicative of a reduction of total body fat of the treated animals.

TABLE II

Antilipogenic Evaluation of Test Compounds - Mouse Study

| Compound | Dosage (ppm) | % Reduction in Fat Pad Weight vs Controls | % Animal Fat vs Controls |
|---|---|---|---|
| 4-amino-3,5-dibromo-α-[(t-butylamino)methyl]benzyl alcohol hydrochloride | 400 | −21.4 | −14.6 |
|  | 200 | −27.5* | −18.4* |
|  | 100 | −13.9* | −5.3* |
| 4-amino-3,5-dibromo-α-[(diisopropylamino)methyl]benzyl alcohol hydrochloride | 200 | −11.1 | −9.4 |
| 4-amino-α-[(t-butylamino)methyl]-3,5-dichlorobenzyl alcohol hydrochloride | 400 | −50.0 | −23.8 |
|  | 200 | −28.1 | −12.1 |
|  | 100 | −37.9 | −14.4 |
| 4-amino-3,5-dichloro-α-[(methylamino)methyl]benzyl alcohol hydrochloride | 200 | −14.7 | −9.9 |
|  | 100 | −8.8 | −11.5 |
| 4-amino-3,5-dichloro-α-[(diethyl)methyl]benzyl alcohol hydrochloride | 200 | −64.7 |  |
|  | 100 | −41.2 |  |
| 4-amino-α-[(sec-butylamino)methyl]-3,5-dichlorobenzyl alcohol | 200 | −56.2 | −36.3 |
|  | 100 | −18.2 | −19.3 |
| 4-amino-3,5-dichloro-α-[(diallylamino)methyl]benzyl alcohol hydrochloride | 200 | −12.0 |  |
| 4-amino-3,5-α-[(benzylamino)methyl]benzyl alcohol hydrochloride | 200 | −17.7 | −5.4 |
|  | 100 | −21.1 | −1.7 |
| 4-amino-α-[(butylamino)methyl]-3,5-dichlorobenzyl alcohol | 200 | −21.54 | −16.78 |
|  | 100 | −24.7 | −13.08 |
| 4-amino-3,5-dichloro-α-[(isopropylamino)methyl]benzyl alcohol | 200 | −50.2 | −25.5 |
|  | 100 | −36.9 | −20.4 |
| α-[(allylamino)methyl]-4-amino-3,5-dichlorobenzyl alcohol | 200 | −16.5 |  |
|  | 100 | −18.3 |  |
| 4-amino-α-[1-(t-butylamino)ethyl]-3,5-dichlorobenzyl alcohol hydrochloride | 100 | −18.8 |  |
| α-[(t-butylamino)methyl]-3,5-dichlorobenzyl alcohol hydrochloride | 200 | −22.5 |  |
|  | 100 | −14.8 |  |
| 4-amino-3-bromo-α-[(t-butylamino)methyl]-5-chlorobenzyl alcohol hydrochloride | 200 | −17.8 |  |
|  | 100 | −18.7 |  |
| m-hydroxy-α-[(isopropylamino)methyl]benzyl alcohol | 400 | −19.8 |  |
|  | 200 | −26.2 |  |
|  | 100 | −7.5 |  |
| 4-amino-N—t-butyl-3,5-dichlorophenethylamine hydrochloride | 50 | −24.8 |  |
| 4-amino-3,5-dichloro-α-[(cyclopropylamino)methyl]-benzyl alcohol | 100 | −30.7 |  |
| 4-[2-(t-butylamino)-1-hydroxyethyl]-2'-chloroacetanilide | 200 | −6.7 |  |
|  | 100 | −12.1 |  |

TABLE II-continued

Antilipogenic Evaluation of Test Compounds - Mouse Study

| Compound | Dosage (ppm) | % Reduction in Fat Pad Weight vs Controls | % Animal Fat vs Controls |
|---|---|---|---|
| 4-amino-3,5-dichloro-α-[(cyclopentylamino)methyl]benxyl alcohol | 200 | −24.5 | |
| | 50 | −4.7 | |
| 4-amino-3,5-dichoro-α-([(2-hydroxyethyl)amino]methyl)-benzyl alcohol | 200 | −15.2 | |
| | 50 | −7.4 | |
| 4-amino-α-[(t-butylamino)methyl]-3,5-diiodobenzyl alcohol hydrochloride | 200 | −32.6 | |
| | 100 | −26.6 | |
| 4-amino-N—t-butyl-3,5-dichloro-β-methoxyphenethylamine hydrochloride | 200 | −13.4 | |
| | 50 | −21.7 | |
| α[(Tert-butylamino)methyl]-3,5-dichloro-4-dimethylamino benzyl alcohol | 200 | −46.1 | |
| | 50 | −14.8 | |
| 4-Amino-3,5-dichloro-α-{[(3-phenyl-propyl)amino]methyl} benzyl alcohol | 200 | −41.1 | |
| | 50 | −36.2 | |
| 4-Amino-3,5-dichloro-α{[(α,α-dimethylphenethyl)amino] methyl}benzyl alcohol hydrochloride | 200 | −13.1 | |
| | 50 | −13.9 | |
| α-[(Tert-butylamino)methyl]-3,5-dichloro-4-methylamino-benzyl alcohol | 200 | −51.0 | |
| | 50 | −41.9 | |
| 4-Amino-N—tert-butyl-3,5-dichloro-β-isoproxyphenethylamine | 200 | −57.0 | |
| | 50 | −17.0 | |
| 4-Amino-N—tert-butyl-3,5-dichloro-β-ethoxyphenethylamine hydrochloride | 200 | −33.7 | |
| | 50 | −15.3 | |
| Methyl-4-{3-[(4-amino-3,5-dichloro-β-hydroxyphenethyl)amino]propyl}benzoate | 200 | −27.7 | |
| | 50 | −14.6 | |
| Methyl-4-[2-tert-butylamino)-1-hydroxyethyl]-2,6-dichlorocarbanilate | 50 | −23.5 | |
| 4'-[2-(tert-butylamino)-1-hydroxyethyl]-2,6-dichlor-acetanilide hydrochloride | 200 | −27.1 | |
| | 50 | −8.8 | |
| 5-[2-tert-butylamino-1-hydrxyethyl]-3-chloranthranilonitrile | 200 | −45.9 | |
| | 50 | −10.4 | |
| 4-amino-β-(benzyloxy)-N—tert-butyl-3,5dichloro-phenethylamine hydrochloride | 200 | −24.2 | |
| | 50 | −18.4 | |
| α-[(tert-butylamino)methyl]-3,5-dichloro-4-isopropylaminobenzyl alcohol | 200 | −52.5 | |
| | 50 | −22.6 | |
| | 12 | −6.3 | |
| | 3 | −25.5 | |
| 4¹-[2-(Tert-butylamino)-1-hydroxyethyl]-2¹,6¹-dichlorovaleranilide | 200 | −33.2 | |
| | 50 | −16.1 | |
| Benzyl-4-[2-(tert-butylamino)-1-hydroxyethyl]-2,6-dichlorocarbanilate | 50 | −19.6 | |
| Methyl-5-[2-(tert-butylamino)-1-hydroxyethyl]-3-chloroanthranilate hydrochloride | 200 | −5.9 | |
| | 50 | −5.8 | |
| 5-[2-(Tert-butylamino)-1-hydroxyethyl]anthranilo-nitrile | 200 | −41.5 | |
| | 50 | −10.3 | |
| 4-[Amino-N—tert-butyl-3,5-dichloro-β-(methylthio) phenethylamine hydrochloride | 200 | −28.9 | |
| | 50 | −16.2 | |
| N—tert-butyl-3,5-dichloro-β-methoxyphenethylamine hydrochloride | 200 | −22.5 | |
| | 50 | −10.4 | |

*Average 2 tests

EXAMPLE 3

Antilipogenic evaluation of test compounds—Rat study

The procedure employed and the diet used for evaluation of test compounds as antilipogenic agents mice, are described in Example 1, excepting that the treatment period is fourteen days and 10 rats, one per cage, are used for each treatment.

Percent body fat is determined in the same manner as described in Example 1, excepting that the skin and organs are removed before the carcasses are homogenized.

Results of this study are reported in Table III below.

TABLE III

Antilipogenic Evaluation of Test Compounds and Growth Rate Evaluation in Rats

| Compound | Level in Diet (ppm) | Number of Rats per Treatment | Average Initial Weight (g) | Average Final Weight (g) | Average Gain per Rat (g) | % Fat in Eviscerated Carcass | Change in Fat from Control |
|---|---|---|---|---|---|---|---|
| $H_2N-\underset{Cl}{\overset{Cl}{\bigcirc}}-\underset{OH}{CH}-CH_2-NH-C(CH_3)_3 \cdot HCl$ | 0 | 10 | 72.7 | 149.1 | 76.4 | 4.67 | — |
| | 25 | 10 | 78.3 | 159.3 | 81.0 | 3.04 | −34.9 |
| | 100 | 9 | 76.6 | 159.8 | 83.2 | 2.54 | −42.0 |
| | 400 | 10 | 73.2 | 146.4 | 73.2 | 2.71 | −45.6 |

EXAMPLE 4

Evaluation of test compounds for increasing the muscle and/or protein in swine and improving the lean meat to fat ratio thereof Barrows, weighing approximately 45 kg are placed in pens and offered swine finishing feed containing 0.2% by weight of a chlortetracycline (50 g/lb) premix in soybean meal, and water ad libitum. When the pigs have reached 57 kg body weight, they are randomly divided into groups of 6 and placed in pens. Four pens per treatment are used for the evaluations.

Control animals are offered an unmedicated finishing feed and water ad libitum throughout the trials. Medicated swine are offered the same diet containing the test drug at the levels indicated in the table below, and water ad libitum. The swine are weighed at the beginning and on completion of the experiment. Feed is weighed each day and unconsumed feed collected recovered and weighed in order to determine the amount of feed consumed.

The experiment is conducted over a 42 day period at the end of which the pigs are sacrificed by stunning and exsanguination. The head is removed and the animals eviserated. The dressed carcass is split in half lengthwise, weighed and hung overnight at 32° F. The split carcass is measured and then cut in cross-section at the 6th–7th rib interface and at the 10th–11th rib interface. The loin eye (longissimus dorsi) cross-sectional area is traced onto paper and the area in the $cm^2$ determined by overlaying a pre-marked grid. The values thus obtained are used to calculate the muscle and fat composition.

Half of each carcass is ground twice in a meat grinder and samples taken and analyzed for protein, moisture and fat.

The diet employed in these tests is as follows:

| DIET SWINE FINISHER | |
|---|---|
| Ingredient | % |
| Corn, Ground | 83.15 |
| Soybean Meal (49%) | 12.50 |
| Meat & Bone Meal (50%) | 2.50 |
| DiCalcium Phosphate (18.5% P) | 0.75 |
| Iodized Salt | 0.50 |
| Limestone (38% Ca) | 0.35 |
| NI Vitamin-Mineral Mix* (Cyanamid) | 0.20 |
| Selenium Premix* (Cyanamid) | 0.05 |
| | 100.00 |

| NI SWINE VITAMIN-MINERAL PREMIX[a] | | |
|---|---|---|
| Furnishes the following per 1000 kg (2200 lb) Diet | | |
| Diet Type | | Finisher |
| NI Premix Added (%) | | 0.20 |
| Vitamins: | | |
| Vitamin A | M.I.U.[b] | 3.52 |
| Vitamin D$_3$ | M.I.U. | .88 |
| Vitamin E | T.I.U.[c] | 2.2 |
| Riboflavin | g | 2.6 |
| d-Pantothenic Acid | g | 7.3 |
| Niacin | g | 17.6 |
| Choline | g | 76. |
| Vitamin B$_{12}$ | mg | 15.4 |
| Menadione (K$_3$) | g | 1.1 |
| Minerals: | | |
| Iodine (I) | g | 2.4 |
| Cobalt (Co) | g | 1.2 |
| Copper (Cu) | g | 4.0 |
| Iron (Fe) | g | 48.0 |
| Manganese (Mn) | g | 24.0 |
| Zinc (Zn) | g | 64.0 |
| Magnesium (Mg) | g | 12.0 |
| Potassium (K) | g | 4.0 |
| SELENIUM PREMIX | | |
| Addition of 0.05% or 0.5 kg per 1000 kg (2200 lb) furnishes 0.1 ppm selenium in the finished diet. | | |

Moisture Determination

Moisture content in the ground carcass samples is determined by weighing out approximately 10 g samples, placing said samples in aluminum foil pans and weighing the samples and pan. These samples are then placed in a forced air oven, dried overnight and the dry weight of the pan and sample determined the following day.

Protein Determination

Protein content is determined by the macro-Kjieldahl method, using 1 g samples of the ground carcass.

Fat Determination

Approximately 5 g samples of the ground carcass are weighed into 50 ml centrifuge tubes. Fifteen ml of concentrated hydrochloric acid are added to each sample and the samples digested by heating at 80° C. for 2 hours.

The samples are then extracted twice with 15 ml of petroleum ether. The samples are agitated in a vortex mixer and then centrifuged at 1500 rpm for 10 minutes. The ether layer is separated from the solids and the ether layers from each extraction combined. The ether is evaporated and the remaining residue weighed to determine the amount of fat in each sample.

Data obtained are reported in Table IV below.

TABLE IV

Evaluation of Test Compounds for Increasing the Muscle and/or Protein in Swine and Improving the Lean Meat to Fat Ratio Thereof Compound
4-amino-α-[(tert-butylamino)methyl]-3,5-dichlorobenzyl alcohol-ppm in diet

| | ppm | | | | |
|---|---|---|---|---|---|
| Av./Pig | 0 | 2 | 10 | 50 | 100 |
| Init. wt. (kg) | 53.5 | 53.8 | 53.6 | 53.8 | 53.2 |
| Final wt. (kg) | 84.0 | 78.6 | 75.4 | 77.8 | 78.9 |
| Total Food Consumption (kg) | 105 | 84 | 84 | 88 | 88 |
| Dressed carcass (kg) | 61.4 | 57.8 | 56.1 | 57.9 | 58.0 |
| Total muscle (kg) | 33.4 | 35.8 | 36.3 | 34.1 | 34.9 |
| Total fat (kg) | 16.4 | 11.1 | 9.9 | 12.5 | 12.1 |
| Feed/muscle | 3.1 | 2.4 | 2.3 | 2.6 | 2.5 |

EXAMPLE 5

Evaluation of test compounds for increasing muscle tissue and/or protein in swine and improving the lean meat to fat ratio thereof The procedures of Example 4 are repeated in all details excepting that the test drug is administered at 0.5, 2 and 10 ppm in the diet. Data obtained are reported in Table V below.

TABLE V

Evaluation of Test Compounds for Increasing Muscle Tissue and/or Protein in Swine and Improving the Lean Meat to Fat Ratio Thereof Compound
4-amino-α-[(tert-butylamino)methyl]-3,5-dichlorobenzyl alcohol-ppm in diet

| | ppm | | | |
|---|---|---|---|---|
| Av/pig | 0 | 0.5 | 2 | 10 |
| Data from 1st two reps (heaviest pigs at initiation of study) | | | | |
| Init. wt. (kg) | 61.9 | 61.8 | 61.8 | 61.9 |
| Final wt. (kg) | 100.0 | 100.2 | 99.1 | 97.6 |
| Days to slaughter | 45 | 51 | 64 | 56 |
| Feed consumption (tot. kg) | 128 | 126 | 129 | 124 |
| N (no. observ.) | 12 | 10 | 11 | 10 |
| Dressed carcass wt. (kg) | 74.98 | 76.98 | 76.95 | 75.45 |
| Total muscle (kg) | 39.94 | 43.25 | 44.35 | 43.85 |
| Total fat (kg) | 20.84 | 19.05 | 17.95 | 17.25 |
| Feed/muscle | 3.21 | 2.91 | 2.91 | 2.83 |
| % improvement | | (+9.4%) | (+9.4%) | (+11.8%) |
| Data from 3rd and 4th reps (lightest pigs at initiation of study) | | | | |
| Init. wt. (kg) | 53.9 | 53.7 | 53.9 | 53.7 |
| Final wt. (kg) | 100.4 | 98.3 | 95.8 | 98.8 |
| Days to slaughter | 56.1 | 63.0 | 69.6 | 70.3 |
| Feed consumption (tot. kg) | 154 | 151 | 150 | 142 |
| N (no. observ.) | 12 | 10 | 8 | 9 |
| Dressed carcass wt. (kg) | 76.2 | 76.5 | 74.9 | 76.1 |
| Total muscle (kg) | 40.0 | 44.2 | 43.7 | 43.9 |
| Total fat (kg) | 21.7 | 19.9 | 17.1 | 17.8 |
| Feed/muscle | 3.85 | 3.42 | 3.43 | 3.24 |
| % improvement | | (+11.1%) | (+10.9%) | (+15.8%) |

EXAMPLE 6

Evaluation of test compounds as animal feed additives for the enhancement of the growth rate of poultry One day old Hubbard X Hubbard Crossbred Chicks, randomly allotted to pens of ten chicks (5 males and 5 females) each.

Eight pens of chicks are used for unmedicated controls, and four pens of chicks are used at each level of drug. The duration of the experiment is 28 days.

The controls are offered at unmedicated diet of Broiler Ration No. 453 (composition given below) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. The thus obtained data are averaged and summarized in Table VI below, wherein the percent improvement in weight gains and feed/gain ratios are given.

| Component | Percent by Weight |
|---|---|
| Ground yellow corn | 53.45 |
| Soybean oil meal (49%) | 28.00 |
| Menhaden fish meal (60%) | 5.0 |
| Corn gluten meal (60%) | 5.00 |
| Dehydrated alfalfa meal (17%) | 2.00 |
| Stablilized fat | 4.00 |
| Dicalcium phosphate | 1.20 |
| Ground limestone | 0.50 |
| Sodium chloride | 0.30 |
| Trace minerals mixture* | 0.05 |
| Vitamin premix** | 0.50 |
| | 100.00 |

| *Trace Mineral Mixture | | 1 lb/ton furnishes |
|---|---|---|
| Manganese | 12.50% | 62.5 ppm |
| Iron | 6.00 | 30.0 |
| Zinc | 5.00 | 25.0 |
| Copper | 0.65 | 3.25 |
| Iodine | 0.35 | 1.75 |
| Cobalt | 0.25 | 1.25 |
| Calcium minimum | 15.30 | |
| Calcium maximum | 17.35 | |

| **Vitamin Premix for 1-ton | Weight in Gram |
|---|---|
| DL Methionine | 453.6 |
| BHT (butylated hydroxy toluene) | 113.6 |
| Vitamin A (30,000 mcg/g) | 100.0 |
| Vitamin D$_3$ (200,000 mcg/g) | 5.0 |
| Vitamin E (20,000 mcg/lb) | 45.4 |
| Riboflavin | 4.0 |
| Niacinamide | 25.0 |

TABLE VI

Mean Weight Gain and Feed: Efficiency of Control and Test Compound - Treated Chicks Thirteen-Day Battery Testing

| Treatment | ppm in Diet | Mean Gain (g) | % Control | F/G | % Improvement over Control |
|---|---|---|---|---|---|
| Control | 0 | 266.5 | — | 1.40 | — |
| 4-Amino-α-[(tert-butylamino)methyl] 3,5-dichlorobenzyl alcohol | 0.3 | 271.8 | +2.0 | 1.40 | 0 |
| | 0.6 | 274.3 | +2.9 | 1.38 | +1.4 |
| | 1.25 | 259.9 | −2.5 | 1.41 | −0.7 |
| | 2.5 | 260.8 | −2.1 | 1.39 | +0.7 |
| | 5.0 | 251.9 | −5.5 | 1.40 | 0 |
| 4-Amino-3,5-dibromo-α-[(tert-butylamino)methyl]benzyl alcohol hydrochloride | 0.3 | 270.8 | +1.6 | 1.40 | 0 |
| | 0.6 | 271.8 | +2.0 | 1.38 | +1.4 |
| | 1.25 | 267.5 | +0.4 | 1.39 | +0.7 |
| | 2.5 | 265.2 | −0.5 | 1.38 | +1.4 |
| | 5.0 | 270.3 | +1.4 | 1.37 | +2.1 |

EXAMPLE 7

Evaluation of test compounds as animal feed additives for the enhancement of growth rate and improvement in feed efficiency of mice.

Four-week old female outbred rats (5-gram range) from Charles River Breeding Laboratories, 251 Ballardvale St., Wilmington, Mass. 01887, are housed 2/cage in air-conditioned rooms (72° F. to 76° F.) with automatically controlled lights, 14 hours on and 10 hours off. The basal diet used in these studies is Purina Laboratory Chow which is supplied ad libitum. Water is also given ad libitum.

Four days after arrival, the animals are weighed and allotted to treatment groups to minimize weight variation. Ten rats are used per treatment group. Drugs are administered in the feed at 2 ppm, 10 ppm and 50 ppm for a period of 12.5 weeks. Animals are weighed weekly and feed consumption corrected for spillage recorded daily. The results of this trial are shown below in Table VII.

TABLE VII

Evaluation of Test Compounds as Animal Feed Additives for the Enhancement of Growth Rate and Improvement in Feed Efficiency - Mice

| Treatment | Dose ppm | Gain[a] (g) | Feed Consumption[b] (g) | Feed/Gain % Improvement |
|---|---|---|---|---|
| Control | | 157 | 1304 | 8.31 |
| 4-Amino-α-(tert-butylaminomethyl)-3,5-dichloro-benzyl alcohol hydrochloride | 2 | 178 (+13.4%) | 1443 (+10.7%) | 8.11 (+2.4%) |
| | 10 | 186 (+18.5%) | 1467 (+11.5%) | 7.89 (+5.1%) |
| | 50 | 175 (+11.5%) | 1394 (+6.9%) | 7.97 (+4.1%) |
| 4-Amino-3,5-dibromo-α-[(tert-butylamino)methyl]-benzyl alcohol hydrochloride | 2 | 164 (+4.5%) | 1362 (+4.5%) | 8.3 (0.1%) |
| | 10 | 185 (+7.8%) | 1459 (+11.9%) | 7.89 (+5.1%) |
| | 50 | 184 (+17.2%) | 1416 (+8.6%) | 7.70 (+7.3%) |

[a]Values given are the total average gain (g) per rat for the entire experimental period.
[b]Values given are the total average feed consumed per rat for the entire experimental period.
Figures in parentheses are % improvement over control.

EXAMPLE 8

Evaluation of test compounds as animal feed additives for (1) the enhancement of the growth rate of poultry, (2) improvement in feed utilization thereby, (3) increase in the deposition of muscle tissue or protein in said birds and (4) improvement in the carcass quality of treated birds The procedure of Example 4 is employed in the following tests, excepting that eight pens of chicks are used for each treatment level, and the drug is administered in the chick diet for three weeks, i.e., from the start of week five through week seven. The experiment is terminated when the birds are seven weeks old. The weight of the chicks is determined at the beginning and on completion of the experiment, and the weight gains and the amount of feed consumed calculated. In addition, 10 males and 10 females from each group are randomly selected and sacrificed by decapitation. These birds were bled, and the feathers and feet removed. The defeathered carcass, with visera intact, were ground. Samples of the ground carcasses were then analyzed for protein, fat and moisture content. The results of these tests are reported in Table VIII below where it can be seen that chicks receiving from 0.25 to 4.0 ppm of the test compound showed an increase in growth rate, improvement in utilization of their feed, increased deposition of muscle tissue or protein and improved overall carcass quality.

Moisture was determined by placing 10 gram samples in aluminum foil pans, and the weights of sample and pan recorded. These samples were dried overnight in a forced air oven, and the dry weight of the pan and sample recorded.

Protein content was determined by a Macro Kjeldahl method, using 1 gram samples of the ground samples.

Fat was determined by digesting 5 gram samples of the ground birds in 50 ml plastic centrifuge tubes and digesting the samples with 5 ml of concentrated hydrochloric acid at 80° C. for 120 minutes. The digested samples were treated with 15 ml of petroleum ether, mixed and centrifuged at 1500 rpm for 10 minutes, and the ether layer separated from the solids. The sample was extracted again in the same manner, and the ether layers mixed. The ether was then evaporated, and the remaining residue weighed to determine the amount of fat in the sample.

TABLE VIII

Evaluation of Test Compound for Increasing the Growth Rate of Poultry, Improving Efficiency of Feed Utilization Thereby, Enhancing the Deposition of Muscle Tissue or Protein Thereof and Improving the Carcass Quality of Said Poultry

| Av/bird | Compound 4-Amino-α-[(tert-butylamino)methyl]-3,5-dichlorobenzyl alcohol (ppm) in diet | | | | | |
|---|---|---|---|---|---|---|
| | 0 | 0.25 | 0.50 | 1.0 | 2.0 | 4.0 |
| Gain (kg) | 1.08 | 1.12 | 1.12 | 1.12 | 1.11 | 1.10 |
| % + control | | +3.7 | +3.7 | +3.7 | +2.8 | +1.8 |
| Feed consumed (kg) | 2.35 | 2.39 | 2.36 | 2.37 | 2.35 | 2.36 |
| % ± control | | +1.7 | +0.4 | +0.9 | 0 | +0.4 |
| FE | 2.21 | 2.14 | 2.13 | 2.13 | 2.13 | 2.15 |
| % + control | | +3.2 | +3.6 | +3.6 | +3.6 | +2.7 |
| % protein ± control: | | | | | | |
| females | | +5.7 | +4.5 | +5.6 | +5.5 | +6.2 |
| males | | +2.5 | +5.9 | +3.2 | +4.3 | +2.3 |
| % fat ± control: | | | | | | |
| females | | −9.0 | −10.0 | −8.5 | −11.5 | −9.0 |
| males | | −8.4 | −8.8 | −14.2 | −13.7 | −10.5 |

EXAMPLE 9

Growth Enhancement, Feed Efficiency Improvement, Increased Deposition of Muscle Tissue and/or Protein and Improvement in Carcass Composition To determine the effect of feeding experimental compounds to ruminants, wether lambs are randomly allotted to pens in groups of four. Five replications per treatment are used. The sheep are weighed and permitted feed and water ad libitum. The feed is weighed daily, and uneaten feed from the previous day is collected and weighed. Test lambs receive the same diet as control animals, but with the addition of experimental compound at a concentration of from 1 to 100 ppm. The tests are conducted for a period of eight weeks at the end of which the lambs are again weighed, and the feed consumed calculated. The lambs are then necropsied. Ten animals per treatment are dressed, and the average cross-sectional area of the longissimus dorsi measured at the 12th rib and at the 7th lumbar vertebra measured. The data obtained are reported in Table IX.

TABLE IX

Evaluation of Test Compound for
Increasing the Growth Rate of Ruminants,
Improving Feed Efficiency and
Enhancing the Deposition of Muscle Tissue

| Av/Animal | Compound 4-Amino-α-[(tert-butylamino)methyl]-3,5-dichlorobenzyl alcohol (ppm) in Diet | | | |
|---|---|---|---|---|
|  | 0 | 1 | 10 | 100 |
| Initial wt. (kg) | 33.0 | 32.9 | 32.4 | 32.5 |
| Final wt. (kg) | 43.9 | 43.1 | 43.4 | 44.2 |
| ADG (g) | 196 | 180 | 195 | 209 |
| % ± control | — | −8.2 | −0.5 | +6.6 |
| kg feed consumed/8-wk. | 87.75 | 79.50 | 82.00 | 77.50 |
| % ± control | — | −9.4 | −6.6 | −11.7 |
| FE | 8.13 | 7.91 | 7.51 | 6.73 |
| % ± control | — | +2.7 | +7.6 | +17.2 |
| Dressed carcass wt. (kg) | 22.79 | 24.24 | 24.39 | 23.49 |
| Muscle cross-sectional area* (am$^2$) | 14.57 | 19.35 | 20.80 | 18.98 |
| % + control | — | +32.9 | +42.8 | +30.3 |

*Average of cross-sectional area of the longissimus dorsi measured at 12th rib and at the 7th lumbar vertebra.

EXAMPLE 10

α-[(Tert-butylamino)methyl]-3,5-dichlorobenzyl Alcohol Hydrochloride

A solution containing 3.5 g of 3,5-dichlorostyrene oxide in 50 ml of absolute ethanol and 20 ml of t-butylamine is heated gently at reflux for 8 hours and the mixture is evaporated to dryness. The clear yellow syrup is dissolved in 75 ml of ethanol and 25 ml of $H_2O$, and the solution is cooled to 5° C. and acidified with 3N HCl. This solution is evaporated to dryness in vacuo and the residual white solid is recrystallized from acetone to afford 2.81 g, m.p. 218°–221° C.

Anal. Calc'd for $C_{12}H_{17}NOCl_2HCl$: C, 48.26; H, 6.08; H, 4.69. Found: C, 48.49; H, 6.17; N, 4.66.

The free base of the title compound is obtained by neutralization of the title compound with aqueous 10% NaOH. Other salts of the free base are then obtained by treatment of the free base in the above-mentioned procedure (aqueous ethanol) with addition of the appropriate acids, such as $H_2SO_4$, $H_3PO_4$, $HNO_3$, $CH_3SO_3H$, toluenesulfonic acid and pamoic acid.

The intermediate 3,5-dichlorostyrene oxide needed for preparing the title compound is made by reducing 28.4 g of 3,5-dichlorophenacyl bromide in 125 ml of absolute ethanol at 5° C. with 8 g of $NaBH_4$, added portionwise. After the addition is completed, the reaction mixture is stirred 16 hours at ambient temperature, which is obtained by gradual melting of the ice bath overnight. The mixture is quenched with 100 ml of $H_2O$, the aqueous mixture is cooled to 5° C., and carefully acidified to pH 3 with concentrated HCl. The mixture is extracted with 300 ml of $CH_2Cl_2$ and the extract is dried over $MgSO_4$, filtered, and evaporated to dryness in vacuo to afford the epoxide as a clear yellow oil.

The phenacyl bromide intermediate for the above-mentioned styrene oxide is prepared by brominating 10 g of 3,5-dichloroacetophenone in 50 ml of $CHCl_3/50$ ml of EtOAc with 23.6 g of $CuBr_2$. The mixture is heated at reflux for 2.5 hours and cooled to room temperature. After stirring for 16 hours at room temperature, the mixture is cooled in ice for 2 hours and filtered. The filter cake is washed with 50 ml of $CHCl_3$ and the combined filtrates are twice decolorized with activated carbon, filtered, and evaporated to dryness in vacuo to afford the orange oil of the 3,5-dichlorostyrene oxide.

EXAMPLE 11

The following 3,5-dichlorophenyl compounds (A) related to the title compound of Example 10 are prepared by the method described in Example 10 by substituting t-butyl amine with $R_2R_3NH$ amines.

| Compound | $R_2$ | $R_3$ | M.P. °C. |
|---|---|---|---|
| 1 | H | i-$C_3H_7$ | 97–103 |
| 2 | H | 2-$C_4H_9$ |  |

EXAMPLE 12

α-[(Tert-butylamino)methyl]-3,5-dibromobenzyl Alcohol Hydrochloride

This title compound is prepared from 3,5-dibromostyrene oxide in the same manner as described in Example 10. The starting materials for this styrene oxide are similarly prepared starting with 3′,5′-dibromoacetophenone.

The corresponding α-[(isopropylamino)methyl]-3,5-dibromobenzyl alcohol hydrochloride is prepared by substituting isopropyl amine for t-butyl amine.

EXAMPLE 13 m-Hydroxy-α-[(isopropylamino)methyl]benzyl Alcohol Hydrochloride

In 135 ml of 95% ethanol, 36.75 g of m-hydroxyacetophenone, 36.5 g of benzyl chloride, 1.75 g of KI, and 24.6 g of $K_2CO_3$ are stirred and heated at reflux for 5 hours. The mixture is cooled, evaporated in vacuo to remove ethanol and 100 ml of $H_2O$ is added. The mixture is then extracted with diethyl ether three times to afford 350 ml of extract, which is further washed with 50 ml of $H_2O$, saturated $NaHCO_3$ solution (2×50 ml), 50 ml of $H_2O$, and 50 ml of brine in succession. The filtrate is dried over $Na_2SO_4$ and evaporated to dryness. The residual oil is distilled to afford 49.13 g of m-benzyloxyacetophenone, b.p. 145°–147° C./0.2 mm. Bromination of 186 g of this acetophenone is accomplished with 349 g of $CuBr_2$ in 1 l of $CHCL_3/1.5$ l of ethanol heated at reflux. A $N_2$ sweep is used to remove HBr generated. After 4 hours, the mixture is filtered and the filter cake is washed with $CHCl_3$ (2×100 ml). The filtrate is evaporated in vacuo to afford an oil, which is dissolved in 200 ml of absolute ethanol (2×50 ml), and dried to afford 64.28 g m-benzyloxyphenacyl bromide, m.p. 57°–58° C. Further cooling of the filtrate affords 34 g. A 64 g-sample of the phenacyl bromide is added to a stirred mixture containing 212 ml of i-propylamine in 425 ml of ethanol under $N_2$ atmosphere at 5° C. The temperature rises to 12° C. and a clear solution is obtained. The solution is poured into ice (2 L) containing 500 ml of concentrated HCl and 1500 ml of $H_2O$. After stirring for 20 minutes, the mixture is filtered and the solid is washed with $H_2O$. On drying this gives 98.64 g, m.p. 200°–203° C. dec. This solid is dissolved in 400 ml of refluxing methanol, 400 ml of isopropyl alcohol is added, and the solution is concentrated to 400 ml. On cooling and collecting crystals, 54.36 of ketoamine melting at 213°–215° dec is obtained. This material (16 g) is added to 150 ml of methanol which contains 2 g of 5% Pd/carbon and hydrogenated in a Paar vessel at 42 p.s.i.g. of $H_2$. The mixture is filtered and the filtrate is evaporated. The residue is mixed with 50 ml of isopropyl alcohol and evaporated to dryness to afford a syrup, which is mixed with 100 ml of ethanol. They crystals are collected, washed with diethyl ether and dried to give 10.77 g, m.p. 129°–132° C., of the title compound.

By substituting tert-butylamine for isopropylamine, m-hydroxy-α-[(tert-butylamino)methyl]benzyl alcohol hydrochloride, m.p. 150°–154° C. dec. is obtained. Substitution of isopropylamine with diisopropylamine, benzylamine and allyamine affords m-hydroxy-α-[(diisopropylamino)methyl]benzyl alcohol, m-hydroxy-α-[(benzylamino)methyl]benzyl alcohol, and m-hydroxy-α-[(allylamino)methyl]benzyl alcohol hydrochlorides, respectively.

EXAMPLE 14

4-Amino-α[(tert-butylamino)methyl]-3,5-diiodobenzyl Alcohol Hydrochloride

In 10 ml of acetic acid, 0.42 g of p-amino-α-[(tert-butylamino)methyl]benzyl alcohol is stirred under $N_2$ atmosphere and 0.48 g of N,N-dichlorobenzenesulfonamide and 0.6 g of NaI are stirred under $N_2$ atmosphere for 20 minutes. After 3 days, the mixture is poured into ice and the mixture is basified with 50% aq. NaOH. This mixture is extracted with $CH_2Cl_2$ (3×25 ml) and chromatographed on a $SiO_2$ plate using 1% $NH_4OH$/20% $CH_3OH$/$CH_2Cl_2$ to afford 0.22 g of the title compound. The reaction is repeated on a larger scale (8×) and the eluted crude product is dissolved in 100 ml of ethanol/10 ml of $H_2O$, stirred and 10% HCl is added to give pH 3. The mixture is evaporated to dryness in vacuo. Isopropyl alcohol is added and the mixture is evaporated to dryness. This process is repeated twice and the residue is crystallized from methanol/isopropyl alcohol by allowing methanol to evaporate until crystals from (methanol is used to dissolve the crude material before isopropyl alcohol is added). On cooling, 2 g of the title compound is obtained melting at 187° C. dec.

Anal. Calc'd for $C_{12}H_{19}ClI_2N_2O$: C,29.02; H,2.86; N,5.64. Found: C, 29.11; H, 3.64; N, 5.64.

EXAMPLE 15

α-[(Tert-butylamino)methyl]-3,5-dichlorobenzyl Alcohol Hydrochloride

An alternate procedure for preparing the title compound and the compounds described in Example 11 is exemplified. Thus, 10 g of 4-amino-α-[(tert-butylamino)methyl]-3,5-dichlorobenzyl alcohol is added to 100 ml of 50–52% $H_3PO_2$ and the mixture is stirred and cooled to 8° C. in ice while 2.77 g of $NaNO_2$ in 15 ml of $H_2O$ is added over 65 minutes. Foaming occurs and is controlled with antifoaming silicone. After 20 minutes, the mixture is stirred 2 hours without cooling. The mixture is then poured into ice-$H_2O$ mixture and 50% aq. NaOH solution is added until the mixture is alkaline. The alkaline mixture is extracted with $CH_2Cl_2$ three times to give 200 ml of solution, which is washed with 25 ml of 2% NaOH and dried over $MgSO_4$ and evaporated to dryness in vacuo to give 9.13 g of brown oil. On standing, the oil solidifies, and it is dissolved in 100 ml of ethanol containing 10 ml of $H_2O$. The solution is acidified to pH 3 with 10% HCl and evaporated to dryness. The residue is treated with 50 ml of isopropyl alcohol and evaporated to dryness. This procedure is repeated to afford an off-white solid which is dissolved in methanol. The solution is evaporated in vacuo to afford a syrup, which is diluted with 50 ml of isopropyl alcohol and allowed to stand. The crystals which form are collected, washed with isopropyl alcohol and dried to yield 7.8 g, m.p. 217°–221° C. dec., of the title compound.

The compound described in Example 6 is similarly prepared. Deamination of 4-amino-3,5-dibromo-α-[(tert-butylamino)methyl]benzyl alcohol affords 3,5-dibromo-α-[(tert-butylamino)methyl]benzyl alcohol, m.p. 249°–251° C. dec.

EXAMPLE 16

4-Amino-3,5-dichloro-β-methoxyphenethylamine hydrochloride

Under $N_2$ atmosphere, 11 g of 4-amino-α-[(tert-butylamino)methyl]-3,5-dichlorobenzyl chloride is added to 75 ml of methanol at 0° C. After 20 minutes, the cooling bath is removed and the reaction mixture is stirred at ambient temperature. After the reaction is completed, the mixture is evaporated to dryness in vacuo. The residue is stirred in 75 ml of $H_2O$ and the mixture is made alkaline with 6N NaOH solution and extracted with $CH_2Cl_2$ (3×50 ml). The organic phases are dried over $MgSO_4$ and evaporated to dryness to afford an orange oil. This oil is dissolved in 150 ml of absolute EtOH and acidified with HCl/isopropyl alcohol solution to pH 2. The solution is evaporated to dryness and the residue is stirred in 75 ml of ethyl acetate. After cooling, this affords a pale yellow solid which is collected to give 6.97 g of the title compound, m.p. 195°–198° C. dec.

Similarly, substitution of ethyl alcohol, isopropyl alcohol, n-butyl alcohol and n-hexyl alcohol affords the corresponding β-ethoxy, β-isopropoxy, n-butoxy, and n-hexyloxy phenethylamine hydrochlorides.

EXAMPLE 17

4-Amino-α-[(tert-butylamino)methyl]-3,5-dichlorobenzyl chloride

Under $N_2$ atmosphere, 27.72 g of 4-amino-α-[(tert-butylamino)methyl]-3,5-dichlorobenzyl alcohol is added to 200 ml of thionyl chloride stirred at 0°–5° C. After addition is completed, the reaction mixture is stirred at ambient temperature for 3 hours. Subsequently, the mixture is evaporated to dryness in vacuo to afford 37.34 g of yellow solid, which is used as is.

EXAMPLE 18

Alternate Procedure for 4-Amino-3,5-dichloro-β-methoxyphenethylamine hydrochloride In 100 ml of methanol, 10 g of 4-amino-α-[(tert-butylamino)methyl]-3,5-dichlorobenzyl alcohol is stirred in an ice bath and dry HCl gas is introduced into the solution. After saturation of the solution, the mixture is stirred at room temperature for an hour and evaporated to dryness. The solid is then stirred in ethyl acetate to afford the title product, which is collected by filtration.

EXAMPLE 19

N-tert-butyl-3,5-dichloro-β-methoxy-4-methylamino-phenethylamine hydrochloride A 7 g sample of α-[(tert-butylamino)methyl]-3,5-dichloro-4-methylaminobenzyl alcohol is added to 70 ml of thionyl chloride under $N_2$ atmosphere and the mixture is stirred for two hours. Excess thionyl chloride is removed in vacuo, and the glassy residue is dissolved in 50 ml of methanol. The solution is stirred for 1.5 hours and evaporated to dryness. The residue is dissolved in 100 ml of $H_2O$ and extracted with 2×50 ml of $CH_2Cl_2$. The aqueous layer is neutralized with solid $NaHCO_3$ and extracted with $CH_2CL_2$. The extract is dried ($MgSO_4$) and evaporated to dryness in vacuo to give 4.1 g of semi-solid, which after trituration with ethyl ether affords 1.07 g of the title compound, mp 220°–221° C.

Similarly, the following ethers are prepared;

$$CH_3NH-\underset{Cl}{\underset{|}{\overset{Cl}{\overset{|}{\bigcirc}}}}-\underset{OR}{\underset{|}{CH}}-CH_2-NH-Bu-t$$

| Alcohol | R |
|---|---|
| ethanol | $C_2H_5$ |
| 1-propanol | 1-$C_3H_7$ |
| 2-propanol | 2-$C_3H_7$ |
| 1-butanol | 1-$C_4H_9$ |
| 2-butanol | 2-$C_4H_9$ |
| 1-hexanol | n-$C_6H_{13}$ |
| benzyl alcohol | benzyl |
| allyl alcohol | allyl |
| 4-methoxybenzyl alcohol | 4-methoxybenzyl |
| 4-chlorobenzyl alcohol | 4-chlorobenzyl |
| 4-nitrobenzyl alcohol | 4-nitrobenzyl |
| 4-methylbenzyl alcohol | 4-methylbenzyl |
| 3,4-dimethylbenzyl alcohol | 3,4-dimethylbenzyl |
| 3,4-dimethoxybenzyl alcohol | 3,4-dimethoxybenzyl |
| 3,4-dichlorobenzyl alcohol | 3,4-dichlorobenzyl |
| 2-chlorobenzyl alcohol | 2-chlorobenzyl |
| 2-methylbenzyl alcohol | 2-methylbenzyl |

EXAMPLE 20

N-tert-Butyl-3,5-dichloro-β-methoxyphenethylamine hydrochloride

A mixture containing 6.55 g of 4-amino-N-tert-butyl-3,5-dichloro-β-methoxyphenethylamine hydrochloride in 66 ml of 50% hypophosphorous acid is cooled to 5° C. and 1.52 g of $NaNO_2$ in 15 ml of $H_2O$ is added dropwise. Rapid foaming occurs from gas evolution and after 0.5 hours at 5° C., the mixture is stirred further at room temperature for two hours. It is then made alkaline with 50% aqueous NaOH solution, and the mixture is kept at below 25° C. with addition of ice. The mixture is extracted with 3×100 ml of $CH_2Cl_2$ and the combined organic phases are washed with 200 ml of brine, dried ($MgSO_4$), and evaporated to dryness in vacuo to give 5.1 g of the title compound in the form of the free base. This product is dissolved in 50 ml of EtOH and acidified at 5° with 4N HCl to afford a light orange precipitate, which is collected. This gives 3.36 g, mp 278°–280° dec, of the title compound which is recrystallized from isopropanol to give 2.35 g, mp 280° C. dec.

Similarly, N-isopropyl-3,5-dichloro-β-methoxyphenethylamine hydrochloride is prepared from 4-amino-N-isopropyl-3,5-dichloro-β-chlorophenethylamine hydrochloride.

EXAMPLE 21

In the manner described in Example 19, the following ethers are prepared by substituting the corresponding alcohols for methanol.

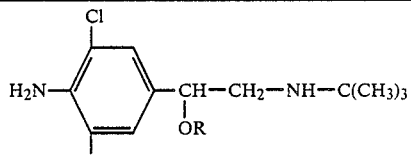

| R | mp°C. |
|---|---|
| Ethyl (.HCl) | 180–182 |
| 2-Propyl | 117–121 |
| benzyl | 190–193 |
| allyl | 57–59 |
| 1-hexyl | |
| 4-methoxybenzyl | |
| 4-chlorobenzyl | |
| 4-nitrobenzyl | |
| 4-methylbenzyl | |
| 3,4-dimethylbenzyl | |
| 3,4-dimethoxybenzyl | |
| 3,4-dichlorobenzyl | |
| phenyl | oil |
| 4-chlorophenyl | |
| 4-methoxyphenyl | |
| 4-methylphenyl | |
| 2-chlorophenyl | |
| 4-nitrophenyl | |

EXAMPLE 22

N-tert-Butyl-3-chloro-5-cyano-β-methoxy-4-amino-phenethylamine hydrochloride In the manner described in Example 19 α-[(tert-butylamino)methyl]-4-amino-3-chloro-5-cyanobenzyl alcohol is converted into the title compound; and, similarly, the following are also prepared:

$$Ar-\underset{OCH_3}{\underset{|}{CH}}-CH_2-NH-R.HCl$$

| Ar | R |
|---|---|
| 4-amino-3,5-dicyanophenyl | t-butyl |
| 4-amino-3-chloro-5-trifluoromethylphenyl | t-butyl |
| 4-amino-3-chloro-5-trifluoromethylphenyl | i-propyl |
| 4-acetamido-3,5-dichlorophenyl | t-butyl |
| 4-acetamidophenyl | t-butyl |
| 4-amino-3-chloro-5-$H_2N$—CO—phenyl | t-butyl |
| 4-amino-3-chloro-5-HO—CO—phenyl | t-butyl |
| 4-amino-3-chloro-5-methyl-phenyl | t-butyl |
| 4-amino-3-chloro-5-methoxy-phenyl | t-butyl |
| 4-amino-3-chloro-5-nitro-phenyl | t-butyl |
| 4-amino-3-chloro-5-$CH_3O$—CO—phenyl | t-butyl |
| 4-amino-3-chloro-5-dimethyl- | t-butyl |

-continued

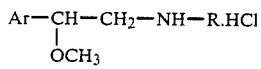

| Ar | R |
|---|---|
| aminomethylphenyl | |
| 4-amino-3-cyano-phenyl | t-butyl |

EXAMPLE 23

5-(4-amino-3,5-dichlorophenyl)-3-tert-butyl-2-oxazolidinone

In 10 ml of $CH_2CL_2$, 0.5 g of 4-amino-α-[(tert-butylamino)methyl]-3,5-dichlorobenzyl alcohol is stirred with 1 ml of $Et_3N$ at $-5°$ C. and 2 ml of 12.5% $COCl_2$ in benzene/5 ml of $CH_2Cl_2$ is added over 15 minutes. The resulting suspension is stirred 20 minutes at 1° C. and allowed to warm to room temperature with stirring for 1.5 hours. The mixture is evaporated to dryness, and the residue is chromatographed on silica gel with 1:1 hexane/$CH_2CL_2$ to afford 0.1 g of oil which crystallizes to give the title compound, mp 97°–103° C.

In the same manner, α-[(allylamino)methyl]-4-amino-3,5-dichlorobenzyl alcohol is allowed to react with phosgene to afford 5-(4-amino-3,5-dichlorophenyl)-3-allyl-2-oxazolidinone.

Likewise, the following compounds are prepared by this manner:

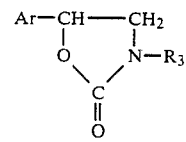

| Ar | $R_3$ |
|---|---|
| 3,5-dichlorophenyl | t-butyl |
| 3,5-dichlorophenyl | i-propyl |
| 4-acetamidophenyl | t-butyl |
| 4-amino-3-chloro-5-cyanophenyl | t-butyl |
| 4-amino-3-chloro-5-trifluoromethylphenyl | t-butyl |
| 3-chloro-4-acetamidophenyl | t-butyl |
| 3,5-dichloro-4-methylaminophenyl | t-butyl |
| 3,5-dichloro-4-methoxy- | t-butyl |
| 3,5-dichloro-4-ethylaminophenyl | t-butyl |
| 3,5-dichloro-4-i-propylaminophenyl | t-butyl |
| 3,5-dichloro-4-acetamidophenyl carbonylaminophenyl | t-butyl |
| 3,5-dichloro-4-benzyloxycarbonylaminophenyl | t-butyl |
| 3,5-dichloro-4-methylcarbamoylaminophenyl | t-butyl |
| 4-amino-3-chloro-5-methylphenyl | t-butyl |
| 4-amino-3-cyanophenyl | t-butyl |
| 4-amino-3-trifluoromethylphenyl | t-butyl |
| 4-amino-3-chloro-5-$NH_2CO$—phenyl | t-butyl |
| 4-amino-3-chloro-5-HOOC—phenyl | t-butyl |
| 4-amino-3-chloro-5-$CH_3OOC$—phenyl | t-butyl |
| 4-amino-3-chloro-5-$(CH_3)_2NCH_2$—phenyl | t-butyl |

-continued

| Ar | $R_3$ |
|---|---|
| 4-amino-3,5-dicyanophenyl | t-butyl |

EXAMPLE 24

4-Amino-α-[(tert-butylamino)methyl]-3,5-dichlorobenzyl alcohol acetate

A mixture containing 1 g of 4-amino-α-[(tert-butylamino)methyl]-3,5-dichlorobenzyl alcohol in 35 ml of $CH_2Cl_2$ at 10°–15° C. is stirred, and 0.37 g of $Ac_2O$ and 0.5 ml of $Et_3N$ are added dropwise. The reaction mixture is then allowed to warm to room temperature, and the reaction is followed by thin-layer chromatography to completion. The mixture is evaporated to dryness in vacuo, and the yellow viscous liquid (1.5 g) is stirred with 50 ml of ethyl ether to afford a yellow solid (0.84 g), mp 128°–131° C. This material is shown by nuclear magnetic resonance spectroscopy and by neutralization with alkali to be the acetic acid salt. On treating 100 mg of this salt in 30 ml of $CH_2Cl_2$ with 30 ml of 10% aqueous NaOH, the salt is neutralized. The $CH_2Cl_2$ solution is dried ($MgSO_4$) and evaporated to dryness in vacuo to afford the viscous title compound. Analysis: Calcd for $C_{14}H_{20}O_2N_2Cl_2$: C, 52.67; H, 6.32; N, 8.78; Found: C, 52.38; H, 6.51; N, 8.88.

In the same manner, propionic anhydride, butyric anhydride, pivalic anhydride, and benzoic anhydride are allowed to react with 4-amino-α-[(tert-butylamino)methyl]-3,5-dichlorobenzyl alcohol (A) and α-[(tert-butylamino)methyl]-3,5-dichloro-4-methylaminobenzyl alcohol (B) respectively, to afford the propionate, butyrate, pivalate and benzoates of A and B.

EXAMPLE 25

The following esters are prepared by the method of Example 24 by using the appropriate acid anhydride.

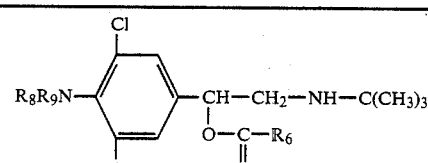

| $R_8$ | $R_9$ | $R_6$ |
|---|---|---|
| H | $CH_3$ | $CH_3$ |
| H | $C_2H_5$ | $CH_3$ |
| H | n-$C_3H_7$ | $CH_3$ |
| H | 2-$C_3H_7$ | $CH_3$ |
| H | benzyl | $CH_3$ |
| H | allyl | $CH_3$ |
| $CH_3$ | $CH_3$ | $CH_3$ |
| H | $CH_3$ | $C_2H_5$ |
| H | $CH_3O$—CO— | $CH_3$ |
| H | $CH_3NH$—CO | $CH_3$ |
| H | $CH_3$ | n-$C_4H_9$ |
| $C_2H_5$ | $C_2H_5$ | $CH_3$ |
| n-$C_4H_9$ | n-$C_4H_9$ | $CH_3$ |

-continued

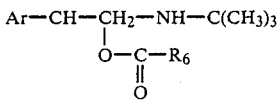

| Ar | R6 |
|---|---|
| 3,5-dichlorophenyl | 2-C3H7 |
| 4-amino-3-chloro-5-cyanophenyl | CH3 |
| 4-amino-3-chloro-5-trifluoro-methylphenyl | CH3 |
| 4-amino-3-chloro-5-H2NCO—phenyl | CH3 |
| 4-amino-3-chloro-5-HOOC—phenyl | CH3 |
| 4-amino-3-chloro-5-methylphenyl | CH3 |
| 4-amino-3-bromo-5-cyanophenyl | CH3 |
| 4-amino-3-chloro-5-CH3OCO—phenyl | CH3 |
| 4-amino-3-chloro-5-(CH3)2NCH2—phenyl | CH3 |
| 4-amino-3,5-dicyanophenyl | CH3 |
| 4-amino-3-cyanophenyl | t-C4H9 |

EXAMPLE 26

N-(4-amino-3,5-dichloro-β-hydroxyphenethyl)-N-tert-butylacetamide acetate

A mixture containing 2.5 g of 4-amino-α-[(tert-butylamino)methyl]-3,5-dichlorobenzyl alcohol, 25 ml of pyridine and 10 ml of acetic anhydride is stirred for three hours and evaporated to dryness in vacuo with heating up to 70° C. The residue is treated with ice, 100 ml of CH2Cl2 and 50 ml of 10% NaOH solution. The CH2Cl2 phase is separated, and the aqueous portion is further extracted with CH2Cl2 (2×50 ml). The combined CH2Cl2 solutions are dried (Na2SO4) and evaporated to dryness to afford a solid after scratching. The solid is washed with hexane and collected to afford 2.61 g of the title compound, mp 126°-136° C.

Similarly, by substituting the appropriate acid anhydrides, the following compounds are prepared.

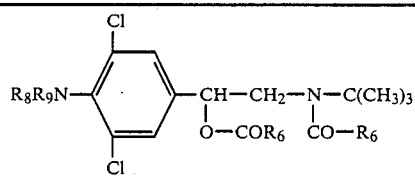

| R8 | R9 | R6 |
|---|---|---|
| H | CH3 | CH3 |
| H | C2H5 | CH3 |
| H | 2-C3H7 | CH3 |
| H | n-C4H9 | CH3 |
| CH3 | CH3 | CH3 |
| H | CH3O—CO | CH3 |
| H | CH3NH—CO | CH3 |
| H | CH3CO | CH3 |
| H | CH3 | C2H5 |
| C2H5 | C2H5 | n-C4H9 |

Ar—CH—CH2—N—C(CH3)3
    |         |
  O—COR6  COR6

| Ar | R6 |
|---|---|
| 4-amino-3,5-dicyanophenyl | C2H5 |
| 4-amino-3-chloro-t-dimethyl-amino methylphenyl | CH3 |
| 4-amino-3-chloro-5-CH3OOC—phenyl | C2H5 |
| 4-amino-3-chloro-5-methylphenyl | CH3 |
| 3,5-dichlorophenyl | CH3 |
| 4-amino-3-chloro-5-cyanophenyl | CH3 |
| 4-amino-3-chloro-5-trifluoro-methylphenyl | CH3 |
| 4-amino-3-chloro-5-H2NCO—phenyl | CH3 |
| 4-amino-3-chloro-5-HO—CO—phenyl | CH3 |

EXAMPLE 27

4-Acetamido-α-[(tert-butylamino)methyl]-3,5-dichlorobenzyl alcohol acetate

In 15 ml of CH2Cl2, 1.57 g of 4-acetamido-β-[(tert-butylamino)methyl]-3,5-dichlorobenzyl alcohol is suspended and stirred while 1.2 g of triethylamine in 30 ml of 30 ml of CH2Cl2 is added, followed by 0.7 g of acetic anhydride in 15 ml of CH2CL2. The mixture is stirred for 20 hours and then is washed with 100 ml of 10% NaOH solution. The organic phase is separated, dried (Na2SO4) and evaporated to dryness in vacuo. The residue is dissolved in 30 ml of ethanol and a trace of H2O is added, followed by 10% HCl to acidify. The mixture is evaporated to dryness in vacuo and the residue is crystallized from acetone/hexane (30 ml/5 ml). This affords 1.35 g, mp. 254°-257° C. dec., of the title compound.

Similarly, by replacing acetic anhydride with propionic anhydride, butyric anhydride, pivalic anhydride, and benzoic anhydride, the corresponding propionate, butyrate, pivalate, and benzoate esters are prepared.

EXAMPLE 28

N-Isopropyl-m-hydroxy-β-methoxyphenethylamine hydrochloride

In 425 ml of ethanol, 64 g of 3-benzyloxyphenacyl bromide and 212 ml of iso-propylamine are stirred at 5° C. under N2 atmosphere, and the temperature is allowed to rise to 12° C. After 0.75 minutes, the clear solution is poured into 2 liters of crushed ice containing 500 ml of concentrated HCl and 1.5 liters of H2O. The mixture is stirred for 20 minutes, filtered and the solid is washed with water to afford 3'-(benzyloxy)-2-isopropylamino-acetophenone hydrochloride, mp 213°-215° C. dec. A 5 g—sample of this material is stirred in 50 ml of methanol, and the mixture is cooled in ice and neutralized with 10% NaOH until a clear solution is obtained. To this solution, 2 g of NaBH4 is added and after 0.75 hours of stirring, the mixture is evaporated in vacuo, and the resulting solid is collected and washed with H2O. This gives, after drying, 4.4 g of m-(benzyloxy)-α-[(isopropylamino)methyl]benzyl alcohol, mp 83°-85° C.

This alcohol is then treated in the manner described in Example 19 to afford N-isopropyl-m-benzyloxy-β-methoxyphenethylamine hydrochloride, which is then debenzylated with H2/5% palladium-carbon at 50 p.s.i.g. in 2-propanol. After filtering and evaporating to dryness, this procedure affords N-isopropyl-m-hydroxy-β-methoxyphenethylamine hydrochloride.

In the same manner, N-tert-butyl-m-hydroxy-β-methoxyphenethylamino hydrochloride is prepared starting with 3'-(benzyloxy)-2-tert-butylaminoacetophenone.

EXAMPLE 29

α-[(tert-Butylamino)methyl]-m-hydroxybenzyl alcohol acetate

In the manner described in Example 27 m-(benzyloxy)-α-[(tert-butylamino)methyl]benzyl alcohol is converted to m-(benzyloxy)-α-[(tert-butylamino)methyl]- benzyl alcohol acetate. This material is then debenzylated by the procedure of Example 28 to give α-[(tert-butylamino)methyl]-m-hydroxybenzyl alcohol acetate.

EXAMPLE 30

5-(p-Aminophenyl)-3-tert-butyl-2-oxazolidinone

In 270 ml of $CH_2Cl_2$, 12.97 g of α-[(tert-butylamino)methyl]-p-nitrobenzyl alcohol is dissolved. The solution is cooled to −5° C. and 54 ml of 12.5% phosgene in benzene is added slowly. After the addition is completed, the mixture is stirred for 3.5 hours and poured on ice. The organic phase is separated, and the aqueous layer is extracted with $CH_2Cl_2$ (2×100 ml). The combined organic layers are washed with saturated $NaHCO_3$ solution (2×250 ml), 100 ml of $H_2O$ and dried over $MgSO_4$. The solution is evaporated to dryness to give 16.3 g, which is recrystallized from MeOH twice to afford 12.58 g of 3-tert-butyl-5-(p-nitrophenyl)-2-oxazolidinone, mp 123°–125° C. This product (10 g) is dissolved in 200 ml of MeOH and hydrogenated over 6 g of Raney nickel at 51 p.s.i.g at 40° C. to give, after filtration and evaporation, 8.21 g of 5-(p-aminophenyl)-3-tert-butyl-2-oxazolidinone, mp 125°–129° C.

EXAMPLE 31

α-[(tert-butylamino)-methyl]B 3,5-dichloro-4-dimethylaminobenzyl alcohol

A mixture containing 50 g of p-fluoroacetophenone and 150 ml of 40% aqueous dimethylamine is warmed in a pressure bottle at 90°–100° C. After two hours, a pale yellow oil is formed. The mixture is cooled, and the oil solidifies. The solid is collected and washed well with $H_2O$ to give 54.93 of p-dimethylaminoacetophenone, mp 101°–103° C., after heptane recrystallization. A 72 g sample of this acetophenone is heated with 129 g of N-chlorosuccinimide in 700 ml of toluene to reflux temperature and maintained at this temperature for 35 minutes. The mixture is cooled and filtered. The filter cake is washed with 200 ml of toluene, and the filtrate and wash solution are evaporated to dryness in vacuo to afford 66 g of oil. This oil is chromatographed on $SiO_2$ with 40% hexane/$CH_2Cl_2$ to give 38.9 g of 3,5-dichloro-4-dimethylaminoacetophenone as a yellow oil. A 5.22 g sample of this oil is added portionwise to 2.75 g of $SeO_2$ in 20 ml of dioxane and 0.7 ml of $H_2O$ at 55°–60° C. This mixture is heated at reflux temperature for 4.5 hours, cooled and filtered through siliceous earth. The filter cake is washed with 20 ml of dioxane. The dioxane solutions are cooled to 15° C. and 2.77 g of t-butylamine is added dropwise to afford a tan precipitate. After stirring 15 minutes at room temperature, the mixture is diluted with 200 ml of ethanol, cooled to 5° C. and 7 g of $NaBH_4$ is added portionwise. After 15 hours, the mixture is treated with 300–400 g of ice and 200 ml of $H_2O$ at below 10° C. The mixture is stirred to dissolve all solids and extracted with 300 ml of $CH_2Cl_2$. The $CH_2Cl_2$ layer is washed with 100 ml of $H_2O$, dried ($MgSO_4$) and evaporated to dryness in vacuo to give 5.6 g of orange oil. This oil is dissolved in ethyl ether, decolorized with activated carbon and concentrated to 15 ml. On cooling, crystals are obtained. The title product is collected as white crystals, mp 96°–99° C.

EXAMPLE 32

5-(4-amino-3,5-dibromophenyl)-3-tert-butyloxazolidine

A mixture containing 2 g of 4-amino-3,5-dibromo-α-[(tert-butylamino)methyl]benzyl alcohol and 5 ml of 37% formalin solution in 20 ml of toluene containing a few crystals of p-toluene sulfonic acid is heated at reflux to azeotrope water. After three hours, the mixture is cooled, diluted to 75 ml with $CH_2Cl_2$ and washed with 10% aqueous NaOH solution (2×20 ml). The aqueous portion is further extracted with 10 ml of $CH_2Cl_2$ and the combined organic extracts are dried ($MgSO_4$) and evaporated to dryness in vacuo to afford 1.6 g of clear brown oil. A chemical ionization mass spectrographic analysis gives a Mass+H+ of 377, which is correct for the title compound. The nuclear magnetic resonance piston spectrum reveals a singlet at δ4.53 in $CDCl_3$ indicative of the O-$CH_2$-N group in the title compound.

In the same manner, the following oxazolidines are prepared by substituting the corresponding arylethanolamines for 4-amino-3,5-dibromo-α-[(tert-butylamino)methyl]benzyl alcohol.

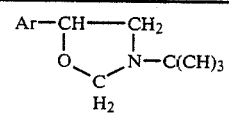

| Ar |
| --- |
| 4-amino-3,5-dichlorophenyl |
| 4-methylamino-3,5-dichlorophenyl |
| 4-amino-3-chloro-5-cyanophenyl |
| 4-amino-3-chloro-5-trifluromethylphenyl |
| 4-amino-3-chloro-5-methylphenyl |
| 4-amino-3-bromo-5-$NH_2$—CO—phenyl |
| 4-amino-3-bromo-5-HOOC—phenyl |
| 4-acetamido-3,5-dichlorophenyl |
| 3,5-dichloro-4-methoxycarbonylaminophenyl |
| 3,5-dichloro-4-methylcarbamoylaminophenyl |
| 4-amino-3-cyanophenyl |
| 4-amino-3-trifluromethylphenyl |
| 4-amino-3,5-dicyanophenyl |

EXAMPLE 33

4-Benzylamino-α-[tert-butylamino)methyl]-3,5-dichlorobenzyl alcohol

In the manner described in Example 31, the title compound is prepared to give mp 86°–89° C.

EXAMPLE 34

4'-[2-(tert-butylamino)-1-hydroxyethyl]-2',6'-dichlorobenzanilide

A mixture containing 2.04 g of 4-amino-3,5-dichloroacetophenone and 0.25 ml of triethylamine in 10 ml of benzoyl chloride is stirred and heated at 130°–135° for two hours. The mixture is cooled, filtered and the product is washed with ether. This amide is further oxidized with $SeO_2$ and further reacted in Example 31 (27) to afford the title compound, mp 177°–182° C.

EXAMPLE 35

α-[tert-butylamino)methyl]-3,5-dichloro-4-methylaminobenzyl alcohol p-Methylaminoacetophenone is prepared and chlorinated by method described in Example 31 to give 3,5-dichloro-4-methylaminoacetophenone. This ketone (18 g) in 200 ml of $CHCl_3$ is stirred and 4.65 ml of $Br_2$ in 50 ml of $CHCl_3$ is added dropwise. After the addition is completed, the mixture is stirred an additional 20 minutes and warmed to reflux temperature for 25 minutes.

The mixture is cooled, 100 ml of H₂O is added and saturated Na₂CO₃ solution is added carefully until the mixture is neutral. The CHCl₃ layer is separated and the aqueous layer is further extracted with 100 ml of CH₂Cl₂. The combined extracts are dried (MgSO₄) and evaporated to dryness to afford 16.3 g of the phenacyl bromide. This material (16 g) in 80 ml of EtOH is stirred at 12°-15° C. and 40 ml of t-butylamine is added dropwise. After the addition is completed the mixture is stirred for 10 minutes at 12°-15° C. and then cooled to 5° and 4 g of NaBH₄ is carefully added. After stirring for 0.5 hours, the mixture is allowed to warm to room temperature and stirring is continued for 0.75 hours. The mixture is poured on 300 ml of ice with stirring and the resulting mixture is extracted with 300 ml of CH₂Cl₂. The CH₂Cl₂ extract is dried (MgSO₄) and evaporated to dryness in vacuo to give a yellow oil. Trituration of this residue with ethyl ether affords 7.45 g of the title compound, which melts at 98°-101° C. after recrystallization from ethyl ether.

EXAMPLE 36

5-[2-(tert-butylamino)-1-hydroxyethyl]anthranilonitrile

A mixture containing 48.86 g of p-aminoacetophenone in 490 ml of toluene is stirred while 64.5 g of N-bromosuccinimide is added in portions over 0.5 hours at below 40° C. After 15 minutes, the mixture is washed with H₂O (4×100 ml). The solution is dried (MgSO₄) and evaporated to dryness to afford 70.53 g of 4-amino-3-bromoacetophenone, mp 59°-62° C. A 35 g sample of this material in 180 ml of dry dimethylformamide is stirred and heated at reflux with 17.57 g of Cu₂(CN)₂ for 6 hours under N₂ atmosphere. Subsequently, 180 ml of FeCl₃/HCl solution (40 g FeCl₃.6H₂O/10 ml concentrated HCl/60 ml H₂) is added and the mixture is heated for 2 minutes at 60°-70° C. and poured into 350 ml of H₂O. The aqueous mixture is extracted with CH₂Cl₂ and the extracts are washed with H₂O, saturated NaHCO₃ solution and H₂O, respectively. The CH₂Cl₂ solution is evaporated to dryness in vacuo and the residue is recrystallized from 95% EtOH to afford 14.25 g, mp 155°-159° C., of 4-amino-3-cyanoacetophenone. A 4.8 g sample of this product in 100 ml of EtOAc and 100 ml of CHCl₃ containing 13.32 g of CuBr₂ is heated at reflux temperature for 20 minutes. The mixture is further heated after 20 ml of EtOH is added and then filtered while still hot. The filter cake is washed with 50 ml of hot 20% MeOH/CH₂Cl₂ and the combined organic solutions are evaporated to dryness in vacuo. The residue is stirred in 25 ml of CH₂Cl₂ and the solid is collected and washed with CH₂Cl₂ to give 8.08 g of the phenacyl bromide. This material is added to 50 ml of t-BuNH₂ in 100 ml of EtOH at 5° under N₂ atmosphere. After 10 minutes of stirring, the mixture is allowed to warm to 30° C. to give a solution. This solution is cooled to 10° and 4 g of NaBH₄ is added in portions. After 45 minutes, the mixture is allowed to warm (42° C.) and kept at 20° C. until the exotherm subsides. The mixture is then evaporated to dryness and the residue is washed with H₂O. The residue is dried and treated with 200 ml of boiling MeOH and the hot MeOH solution is filtered. The filter cake is further washed with hot MeOH and the combined filtrates are concentrated to afford crystals. This solid is recrystallized from MeOH/2-PrOH to afford 2.08 g, mp 184°-186° C., of the title compound.

In a similar manner, the following related compounds are prepared starting with the appropriate acetophenone:

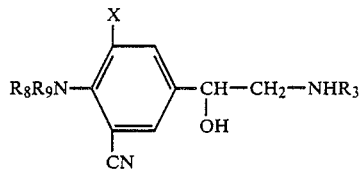

| R₈ | R₉ | R₃ | X |
|---|---|---|---|
| H | H | 2-C₃H₇ | H |
| H | CH₃ | t-butyl | H |
| CH₃ | CH₃ | t-butyl | H |
| H | C₂H₅ | t-butyl | H |
| H | n-C₃H₇ | t-butyl | H |
| H | 2-C₃H₇ | t-butyl | H |
| H | n-C₄H₉ | t-butyl | H |
| H | CH₃ | 2-C₃H₇ | H |
| H | benzyl | t-butyl | H |
| C₂H₅ | C₂H₅ | t-butyl | Cl |
| n-C₃H₇ | n-C₃H₇ | t-butyl | Cl |
| n-C₄H₉ | n-C₄H₉ | t-butyl | Cl |

EXAMPLE 37

3-chloro-5-[2-(tert-butylamino)-1-hydroxyethyl]anthranilonitrile

In 100 ml of toluene, 5 g of 4-amino-3-cyanoacetophenone is heated at reflux temperature for 20 minutes with 4.2 g of N-chlorosuccinimide. The mixture is cooled and filtered. The filtrate is further heated at reflux temperature for 2 hours. The precipitate is collected and washed with H₂O. The remaining solid is treated with 0.75 ml of Br₂/14 ml of CHCl₃ added to 75 ml of CHCl₃ and 4.9 ml of EtOH. The mixture is evaporated to dryness and the residue is slurried with CH₂Cl₂, collected and washed with CH₂Cl₂ to afford 2.84 g of the phenacyl bromide. This material is allowed to react with t-BuNH₂ and reduced with NaBH₄ by the procedure of Example 36 to afford the title compound, mp 128°-138° C.

In a similar manner, the following compounds are prepared:

| R₈ | R₉ | R₃ |
|---|---|---|
| H | H | 2-propyl |
| H | CH₃ | t-butyl |
| CH₃ | CH₃ | t-butyl |
| H | C₂H₅ | t-butyl |
| H | 2-propyl | t-butyl |
| H | n-butyl | t-butyl |
| H | benzyl | t-butyl |

EXAMPLE 38

5-[2-(tert-butylamino)-1-hydroxyethyl]-3-chloroanthranilic acid, methyl ester, hydrochloride A mixture containing 1.36 g of 5-[2-(tert-butylamino)-1-hydroxyethyl]-3-chloroanthranilonitrile in 21 ml of 50% aqueous NaOH and 21 ml of EtOH is stirred under $N_2$ for 0.5 hours. The mixture is evaporated to remove EtOH and acidified to pH 3 and further evaporated to dryness in vacuo. The residue treated several times with MeOH and evaporated to dryness. The solid is then treated with a solution which is prepared from 40 ml of MeOH and 2 ml of acetyl chloride. After allowing to stand overnight, the mixture is filtered and the filtrate is evaporated to dryness. The filter cake is also washed with MeOH and added to preceding filtrate. The residue is dissolved in acetone, filtered, and evaporated to dryness. The solid is triturated with $Et_2O$ and filtered to give 1.49 g, mp 95°–115° C., of the title compound.

In a similar manner, the following related esters are prepared:

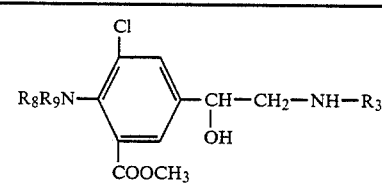

| $R_8$ | $R_9$ | $R_3$ |
|---|---|---|
| H | H | 2-propyl |
| H | $CH_3$ | t-butyl |
| $CH_3$ | $CH_3$ | t-butyl |
| H | $C_2H_5$ | t-butyl |
| H | n-propyl | t-butyl |
| H | n-butyl | t-butyl |
| H | benzyl | t-butyl |
| H | allyl | t-butyl |
| $C_2H_5$ | $C_2H_5$ | t-butyl |
| $n-C_4H_9$ | $n-C_4H_9$ | t-butyl |
| $n-C_3H_7$ | $n-C_3H_7$ | t-butyl |

EXAMPLE 39

2-Amino-3-bromo-5-[2-(tert-butylamino)-1-hydroxyethyl]benzamide

A mixture containing 1.02 g of 3-bromo-5-[2-(tert-butylamino)-1-hydroxyethyl]anthranilonitrile in 25 ml of $H_2O$, 5 ml of 50% NaOH and 30 ml of EtOH is stirred and heated at 55°–65° C. under $N_2$ atmosphere for 1.25 hours. The mixture is evaporated to remove EtOH and extracted with $CHCl_3$. The $CHCl_3$ extract is washed with 25 ml of 2% NaOH, dried ($MgSO_4$) and evaporated to dryness to afford 0.74 g. This solid is stirred with pentane and filtered to afford 0.6 g, mp 135°–145° C., of the title compound.

Similarly, the following compounds are prepared:

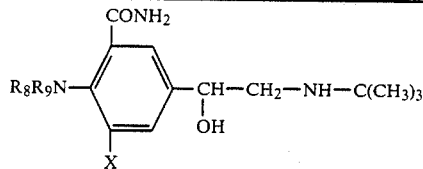

| $R_8$ | $R_9$ | X |
|---|---|---|
| H | $CH_3$ | Cl |
| H | H | Cl |
| H | $C_2H_5$ | Cl |
| $CH_3$ | $CH_3$ | Cl |
| H | $2-C_3H_7$ | Cl |
| H | $n-C_4H_9$ | Cl |
| H | $CH_3$ | Br |
| H | benzyl | Cl |
| $C_2H_5$ | $C_2H_5$ | Cl |
| $n-C_3H_7$ | $n-C_3H_7$ | Cl |
| $n-C_4H_9$ | $n-C_4H_9$ | Cl |

EXAMPLE 40

3-bromo-5-[2-(tert-butylamino)-1-hydroxyethyl]anthranilic acid

A mixture containing 2 g of 3-bromo-5-[2-(tert-butylamino)-1-hydroxyethyl]anthranilonitrile in 10 ml of 50% NaOH, 50 ml of $H_2O$ and 60 ml of EtOH is stirred and heated to reflux temperature under $N_2$ for an hour. The EtOH is evaporated and the aqueous mixture mixed with 50 ml of $H_2O$ and 50 ml of $CHCl_3$. The $CHCl_3$ layer is removed and the interfacial brown oil is collected, added to 10 ml of MeOH, 5 ml of $H_2O$ and this mixture is acidified to pH 5. After stirring for an hour, the off-white solid is collected, washed with $H_2O$ and dried to give 0.8 g, mp 221.5° C. dec., of the title compound.

Similarly, the following compounds are prepared:

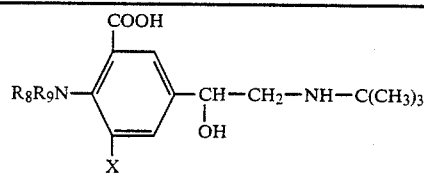

| $R_8$ | $R_9$ | X |
|---|---|---|
| H | H | Cl |
| H | $CH_3$ | Cl |
| $CH_3$ | $CH_3$ | Cl |
| H | $CH_3$ | Br |
| H | $2-C_3H_7$ | Cl |
| H | $n-C_4H_9$ | Cl |
| H | benzyl | Cl |
| $C_2H_5$ | $C_2H_7$ | Cl |
| $n-C_3H_7$ | $n-C_3H_7$ | Cl |
| $n-C_4H_9$ | $n-C_4H_9$ | Cl |

EXAMPLE 41

5-(3-hydroxyphenyl)-3-tert-butyl-2-oxazolidinone

In the manner described in Example 23, m-benzyloxy)-α-[tert-butylamino)methyl]benzyl alcohol is converted to the oxazolidinone compound by treatment with phosgene. Subsequently debenzylation is completed by the method of Example 28 to give the title compound.

EXAMPLE 42

5-(3-hydroxyphenyl)-3-tert-butyloxazolidine

In the manner described in Example 32, m-(benzyloxy)-α-[(tert-butylamino)methyl]benzyl alcohol is reacted with formaldehyde to afford the oxazolidine derivative, which is debenzylated by the procedure of Example 28 to give the title compound.

EXAMPLE 43

4-amino-N-tert-butyl-3,5-dichloro-β-(methylthio)-phenethylamine hydrochloride In the manner described in Example 19, N-tert-butyl-3,5-dichloro-β-chloro-4-aminophenethylamine hydrochloride is prepared. An 11 g sample of this product is portionwise added to 5 ml of methyl mercaptan in 100 ml of dry ethylenedichloride at −10° C. to 0° C. The mixture is stirred and allowed to rise gradually to room temperature over a four day period. The mixture is filtered, the filter cake is washed with ethylenedichloride (2×500 ml). The solid is dispersed in 200 ml of H₂O, cooled to 5° C. and basified with 6N NaOH solution to give a white oil, which is extracted with CH$_2$Cl$_2$ (3×100 ml). The CH$_2$Cl$_2$ extract is dried (MgSO$_4$) and evaporated to dryness to give 6.41 g of dark green oil. This oil is stirred in HCl/isopropanol and the mixture is evaporated to dryness. The residue is stirred in 35 ml of ethyl ether for 16 hours and filtered to give 3.63 g, mp 178°–181° C. dec. This solid is heated in refluxing ethyl acetate and filtered to give 2.07 g- mp 188°–193° C. Recrystallization from 75 ml of ethylenedichloride affords 1.45 g of the title compound, mp 191°–196° C.

The title compound is also obtained by adding 5–10 fold excess of sodium mercaptide in tetrahydrofuran at 0°–10° C. and by following the above workup.

EXAMPLE 44

In the same manner as described in Example 43, the following thioethers are prepared by substituting methyl mercaptan with the corresponding mercaptans:

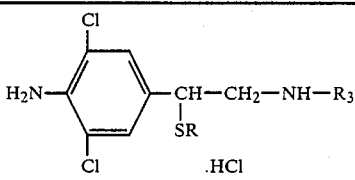

| R | R$_3$ |
|---|---|
| methyl | 2-propyl |
| ethyl | t-butyl |
| 2-propyl | t-butyl |
| n-butyl | t-butyl |
| t-butyl | t-butyl |
| n-hexyl | t-butyl |
| phenyl | t-butyl |
| benzyl | 2-propyl |

EXAMPLE 45

In the manner described in Example 43, substitution of the corresponding chloro compound for N-tert-butyl-3,5-dichloro-β-chloro-4-aminophenethylamine hydrochloride and using the appropriate mercaptans affords the following thioethers:

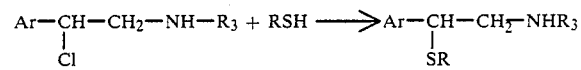

| Ar | R | R$_3$ |
|---|---|---|
| 4-amino-3-cyanophenyl | methyl | 2-propyl |
| 4-methylamino-3,5-dichlorophenyl | methyl | t-butyl |
| 4-amino-3-chloro-5-trifluoromethyl | methyl | t-butyl |
| 4-amino-3-chloro-5-cyanophenyl | methyl | t-butyl |
| 4-amino-3-chloro-5-cyanophenyl | ethyl | t-butyl |
| 4-acetamido-3,5-dichlorophenyl | methyl | t-butyl |
| 4-amino-3-chloro-5-H$_2$NCO—phenyl | methyl | t-butyl |
| 4-amino-3-chloro-5-HOCO—phenyl | methyl | t-butyl |
| 4-amino-3-chloro-5-methylphenyl | ethyl | t-butyl |
| 4-amino-3-chloro-5-methoxyphenyl | n-butyl | t-butyl |
| 4-amino-3-chloro-5-nitrophenyl | methyl | t-butyl |
| 4-amino-3-chloro-5-CH$_3$O—CO—phenyl | methyl | t-butyl |

EXAMPLE 46

3,5-dichloro-4-(N,N-diethylamino)acetophenone

A sample (2.5 g) of 4-amino-3,5-dichloroacetophenone in 10 ml of acetic anhydride and 25 ml of pyridine is stirred and heated at reflux temperature for 20 hours. The mixture is evaporated to dryness, and the residue is treated with ice and 10% NaOH solution and extracted with CH$_2$Cl$_2$ (3×50 ml). The extracts are dried (Na$_2$SO$_4$) and evaporated to dryness to give 2.42 g of semisolid, which is purified by chromatography over SiO$_2$ using CH$_2$Cl$_2$ as eluent to afford 1.06 g of 4-(N,N-diacetyamino)-3,5-dichloroacetophenone as an oil. This material is dissolved in 10 ml of tetrahydrofuran (THF) under N$_2$ atmosphere and 18 ml of 1M BH$_3$.THF is added dropwise. The mixture is stirred until the reaction is complete and H$_2$O is added cautiously. The mixture is evaporated to remove THF and 20 ml of H$_2$O and 10 ml of 10% NaOH are added. This aqueous mixture is extracted with CH$_2$Cl$_2$ (3×25 ml) and the extracts are dried (Na$_2$SO$_4$) and evaporated to dryness to yield 0.68 g the desired alcohol. This product (0.3 g) in 2 ml of CH$_2$Cl$_2$ is added to 0.32 g of pyridinium chlorochromate (PCC) in 2 ml of CH$_2$Cl$_2$. After 1.25 hours, an additional 0.3 g of PCC is added and after another 0.5 hours, the solution is decanted and the residue is washed with 10 ml of CH$_2$Cl$_2$. The combined CH$_2$Cl$_2$ solutions are diluted with 50 ml of CH$_2$Cl$_2$ and washed with 10 ml of saturated Na$_2$CO$_3$ solution and 10 ml of H$_2$O and dried (Na$_2$SO$_4$). The solution is evaporated to dryness to afford a residue which is chromatographed on SiO$_2$ with CH$_2$Cl$_2$ as eluent to yield 0.04 g of the title compound as an oil (NMR in CDCl$_3$: δ1.0 (6H, triplet), 2.5 (3H, singlet), 3.25 (4H, quartet), 7.83 (2H, singlet). The monoethylaminoacetophenone is also obtained as a solid (0.12 g) as the second component.

This 3,5-dichloro-ethylaminoacetophenone is further reacted with propionic anhydride, reduced and reoxidized in the above manner to afford 3,5-dichloro-N-ethyl-N-propylaminoacetophenone.

In a similar manner the following 4-(N,N-dialkylamino-acetophenones which are required for preparing 4-(N,N-disubstituted amino) compounds of formula I are prepared:

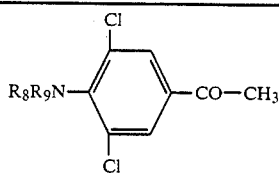

| R$_8$ | R$_9$ | X | Y |
|---|---|---|---|
| n-C$_3$H$_7$ | n-C$_3$H$_7$ | Cl | Cl |
| n-C$_4$H$_9$ | n-C$_4$H$_9$ | Cl | Cl |
| C$_2$H$_5$ | n-C$_3$H$_7$ | Cl | Cl |
| C$_2$H$_5$ | C$_2$H$_5$ | Cl | CH$_3$ |
| C$_2$H$_5$ | C$_2$H$_5$ | Cl | CF$_3$ |
| C$_2$H$_5$ | C$_2$H$_5$ | Cl | NO$_2$ |
| C$_2$H$_5$ | C$_2$H$_5$ | Cl | Br |
| C$_2$H$_5$ | C$_2$H$_5$ | Cl | OCH$_3$ |

EXAMPLE 47

α-[(tert-butylamino)methyl]-3,5-dichloro-4-diethylaminobenzyl alcohol

In the manner described in Example 31, 3,5-dichloro-4-diethylaminoacetophenone is oxidized with SeO$_2$ and reductively alkylated with t-BuNH$_2$/NaBH$_4$ to afford the title compound, mp 93°–96° C.

Similarly, α-[tert-butylamino)methyl]-3,5-dichloro-4-(n-dipropyl)aminobenzyl alcohol and α-[(tert-butylamino)methyl]-3,5-dichloro-4-(n-dibutyl)aminobenzyl alcohol are prepared.

EXAMPLE 48

2-bromo-3′,5′-dichloro-4′-diallylaminoacetophenone
and
4′-(allylamino)-2-bromo-3′,5′-dichloroacetophenone

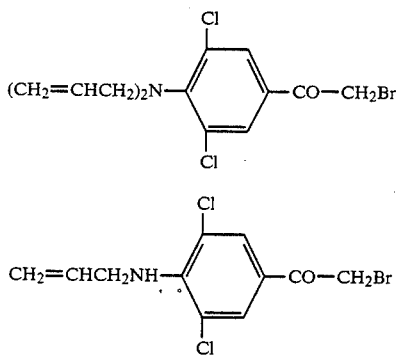

Triethylamine (17.0 g, 0.168 mol) is added in one portion to allyl bromide (105.9 g, 0.875 mol) under a nitrogen atmosphere. The resulting white emulsion gives an exotherm to 70° C. and becomes a thick white solid mass within 5 minutes. The solution formed with the addition of ~100 ml of DMF is stirred for 1 hour at 70°–95° C. A solution of 4′-amino-2-bromo-3′,5′-dichloroacetophenone (25.0 g, 0.088 mol) in 50 ml of DMF is added in one portion and the resulting brown reaction mixture is maintained at 80°–90° C. for 2 hours. The progress of the reaction is frequently checked by thin layer chromatography SiO$_2$/CH$_2$Cl$_2$/hexanes (1/1)) since prolonged heating results in the decomposition of both starting material and products. The reaction mixture is poured into 1.5 l of H$_2$O and is stirred for 0.5 hours. After a second aqueous trituration, the residual brown semi-solids are stirred with ~150 ml of CCl$_4$ for 0.5 hours to form a suspension. The yellowish-brown solids are collected by filtration and are air dried to give 14.9 g (59.6%) of recovered phenacyl bromide starting material. The CCl$_4$ filtrate is stirred with MgSO$_4$, filtered and concentrated to yield 9.42 g of a brown syrup. Gradient elution (hexanes/CH$_2$Cl$_2$ (10/0→8/2) flash chromatography on a 9″×2″ column of Silica Gel 60 gives two major fractions:

(A) 1.82 g (5.7%) of a faster moving amber syrup, identified as 2-bromo-3′,5′-dichloro-4′-diallylaminoacetophenone by IR(neat) 1680 cm$^{-1}$; NMR (CDCl$_3$) δ7.93 (s, 2, AR—H), 6.25-5.55 (complex m, 2, CH═), 5.40-4.95 (complex m, 4, CH$_2$═), 4.40 (s, 2, CH$_2$Br) and 3.87 (m resembling d, 4, J=6 Hz, (CH$_2$N); chemical ionization mass spectrum (M+H)$^+$=3.62; and (B) 3.49 g (12.2%) of a slower moving brown syrup, ideitified as 4′-(allyamino)-2-bromo-3′,5′-dichloroacetophenone by IR(neat) 3330, 1670 cm$^{-1}$; NMR(CDCl$_3$) δ7.83 (s, 2, AR—H), 6.35-5.65 (complex m, 1, CH═), 5.50-5.00 (complex m, 2, CH$_2$═), 4.84 (br t, 1, NH), 4.37 (s, 2, CH$_2$Br) and 4.20 (br m, 2, CH$_2$N); chemical ionization mass spectrum (M+H)$^+$=322.

EXAMPLE 49

4-(Allyamino)-α-[(tert-butylamino)methyl]-3,5-dichlorobenzyl alcohol

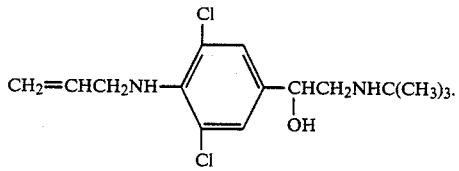

A solution of 4′-(allylamino)-2-bromo-3′,5′-dichloroacetophenone (2.88 g, 8.92 mmol) in 10 ml is added dropwise over 1 hour to a stirred solution of t-butylamine (1.34 g, 18.3 mmol) in 20 ml of THF. The reaction temperature is maintained at −24°–13° C. by cooling in a dry ice-CCl$_4$ bath. The resulting amber suspension is warmed to room temperature over 30 minutes and is stirred at <°–22° C. for 1.5 hours. Sodium cyanoborohydride (2.80 g, 44.6 mmol) is added in two portions over 5 minutes to give a thick tan suspension with an exotherm from 22°–25° C. Glacial acetic acid (~10 ml) is added dropwise to gradually form a yellow solution which is stirred at room temperature for 3 days. The reaction mixture is poured into a solution of 100 ml of H$_2$O and 100 ml of saturated aqueous NaCl which is then adjusted to pH7 with 10% Na$_2$CO$_3$ and extracted three times with Et$_2$O. The combined extracts are shaken with two portions of diluted aqueous HCl which are combined, neutralized with 10% Na$_2$CO$_3$ to pH8 and extracted three times with Et$_2$O. After stirring the combined extracts with anh. K$_2$CO$_3$, the pale yellow-green solution is filtered and concentrated to yield 2.04 g (72.1%) of a pale yellow syrup, identified as 4-(allylamino)-α-[(tert-butylamino)methyl]-3,5-dichlorobenzyl alcohol by IR(neat) 3400 cm$^{-1}$; NMR(CDCl$_3$) δ7.32 (s, 2, Ar—H), 6.35-5.60 (complex m, 1, CH═), 5.45-4.95 (complex m, 2, CH$_2$═), 4.52 (d of d, 1, Ar—CH), 3.97 (overlapping m, 3, Ar—NHCH$_2$), 3.03 (br s, 2, NH and OH), 2.68 (m, 2, CH$_2$N) and 1.13 (s, 9, C(CH$_3$)$_3$); chemical ionization mass spectrum (M+M)$^+$=317. The CH₂Cl₂/CH₃OH/conc. NH₄OH (80/19/1)) shows one major spot (R_f=0.6) with nine trace impurities. The syrup gradually crystallizes to a tan solid on standing.

EXAMPLE 50

N-tert-butyl-m-hydroxy-β-methylthiophenethylamine hydrochloride

By using the procedure of Example 28 and substituting methyl mercaptan for methanol as in Example 43, the title compound is prepared.

EXAMPLE 51

The following compounds are prepared by the method of Example 31:

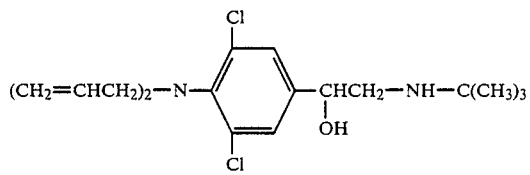

| R₈ | R₉ | mp °C. |
|---|---|---|
| H | 1-C₄H₉ | oil |
| H | 1-C₆H₁₃ | 62–64 |
| H | C₂H₅ | 209 (HCl salt) |
| H | benzyl | 85–89 |
| H | cyclopentyl | oil |
| H | cyclohexyl | 194–198 (HCl salt) |
| —CH₂—CH₂—CH₂—CH₂— | | |

EXAMPLE 52

α-[(tert-butylamino)methyl]-3,5-dichloro-4-diallylaminobenzyl alcohol

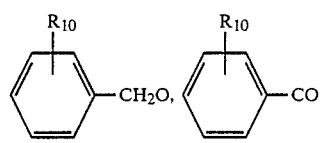

The title compound is prepared using the procedure described for the preparation of 4-(allylamino)-α-[(tert-butylamino)methyl]-3,5-dichlorobenzyl alcohol (Example 49). The pale yellow syrup, which gradually crystallizes on standing, is identified by IR(neat) 3300 and 1630 cm⁻¹; NMR(CDCl₃) δ7.26 (s, 2, AR—H), 6.23–5.54 (complex m, 2, CH=), 5.32–4.87 (complex m, 4, CH₂=), 4.48 (m, 1, Ar—CH), 3.78 (m resembling d, 4, J-6 Hz, Ar—NCH₂), 3.4–2.0 (br s, 2, NH and OH), 2.62 (m, 2, CH₂N) and 1.13 (s, 9, C(CH₃)₃); chemical ionization mass spectrum (M+H)⁺=357, corresponding to that expected of the title compound.

I claim:

1. A method for increasing lean meat, improving the lean meat to fat ratio, reduction of body fat and improving the efficiency of feed utilization, or increasing the growth rate in warm-blooded animals comprising: orally or parenterally administering to said animals, a pharmacologically effective amount of a compound having the general formula selected from the group consisting of;

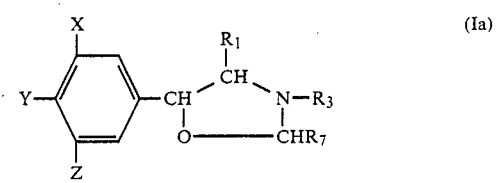

and

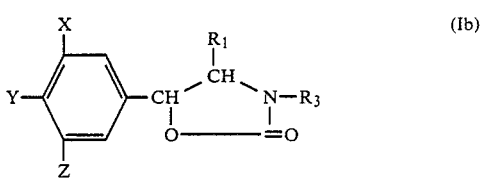

wherein X is hydrogen, halogen, or —CN; Y is hydrogen, NR₈R₉ or NHCOR₅; Z is halogen, OH, CF₃, CN, COOR₁, CONH₂, C₁–C₄ alkyl, C₁–C₄ alkoxy, nitro or C₁–C₄ dialkylaminomethyl; R₁ is hydrogen or C₁–C₄ alkyl; R₃ is C₁–C₅ alkyl, C₃–C₄ alkenyl, C₃–C₅ cycloalkyl, 2-hydroxyethyl, α,α-dimethylphenethyl, benzyl, 3-phenylpropyl or 3-(4-carbomethoxyphenyl)propyl; R₅ is hydrogen, C₁–C₄ alkyl, C₁–C₄ alkoxy, or N(R₁)₂; R₇ is hydrogen, C₁–C₄ alkyl or phenyl; R₈ is hydrogen, C₁–C₄ alkyl or C₃–C₄ alkenyl; R₉ is hydrogen, C₁–C₆ alkyl, C₄–C₆ cycloalkyl, C₃–C₄ alkenyl or benzyl; R₁₀ is hydrogen, chloro, dichloro, methyl, dimethyl, methoxy, dimethoxy or nitro; and when R₈ and R₉ are taken together with the nitrogen to which they are attached, they may represent pyrrolidino; with the provisos that when Z is OH, X and Y are hydrogen; when X is —CN, Z is —CN; and when R₈ is C₁–C₄ alkyl or C₃–C₄ alkenyl, R₉ is C₁–C₄ alkyl or C₃–C₄ alkenyl; or racemic mixtures of the above-identified compounds, the optically active isomers, or nontoxic, pharmacologically acceptable acid addition salts thereof.

2. A method according to claim 1 wherein said warm blooded animals are selected from the group consisting of swine, poultry, sheep, goats, domestic pets and cattle; and said compound is orally administered to said animals in an animal feed containing from 0.01 to 400 grams of said compound per ton of feed.

3. The method according to claim 1 wherein said warm blooded animals are selected from the group consisting of swine, poultry, sheep, goats, domestic pets and cattle; and said compound is parenterally administered as a subcutaneous implant containing a sufficient amount of said compound to provide said animals with from 0.001 to 100 mg/kg/day of body weight of said compound.

4. The method according to claim 2 wherein said animals are swine and said animal feed contains from 50 to 300 grams per ton of said compound.

5. The method according to claim 2 wherein the animal is poultry and the feed contains from 10 to 400 grams per ton of the active compound.

6. The method according to claim 3 wherein said animals are swine and are treated by subcutaneous injection of an implant composition containing sufficient compound to provide said animals with from 0.001 to 100 mg/kg/day of body weight of said compound.

7. The method according to claim 3 wherein said animals are poultry and are treated by subcutaneous injection of an implant composition containing from 0.001 to 35 mg/kg/day of body weight of said active compound.

8. The method according to claim 2 wherein said animals are cattle or sheep and said animal feed contains from 50 to 300 grams per ton of feed.

9. The method according to claim 1 wherein the meat producing animals are swine and the animal feed contains from 0.01 to 400 grams of compound per ton of feed is administered to said swine weighing at least 30 kg body weight.

10. The method according to claims 1, 2, 3, 4, 5, 6, or 7, wherein said compound is (Ib) and $R_3$ is tert-butyl or tert-propyl.

11. The method according to claim 10, wherein said compound is 5-(4-amino-3,5-dichlorophenyl)-3-tert-butyl-2-oxazolidinone or a non-toxic, pharmaceutically acceptable acid addition salt thereof.

12. The method according to claims 1, 2, 3, 4, 5, 6, or 7, wherein said compound is (Ia), $R_7$ is hydrogen, and $R_3$ is tert-butyl.

13. The method according to claim 12, wherein said compound is 5-(4-amino-3, 5-dibromophenyl)-3-tert-butyloxazolidine or a non-toxic, pharmaceutically acceptable acid addition salt thereof.

14. The method according to claims 1, 2, 3, 4, 5, 6, or 7, wherein said compound is 5-(3-hydroxyphenyl)-3-tert-butyl-2-oxazolidinone or a non-toxic, pharmaceutically acceptable acid addition salt thereof.

15. The method according to claims 1, 2, 3, 4, 5, 6, or 7, wherein said compound is 5-(3-hydroxyphenyl)-3-tert-butyl-oxazolidine or a non-toxic, pharmaceutically acceptable acid addition salt thereof.

16. A method for increasing lean meat, improving the lean meat to fat ratio, reduction of body fat and improving the efficiency of feed utilization, and increasing the growth rate in warm-blooded animals comprising: orally or parenterally administering to said animals, a pharmacologically effective amount of the compound having the general formula selected from the group consisting of;

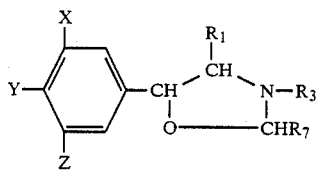
(Ia)

and

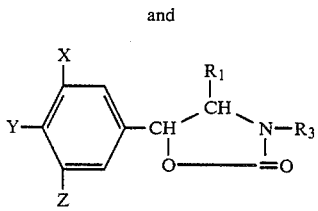
(Ib)

wherein X is hydrogen, halogen or —CN; Y is hydrogen, $NR_8R_9$ or $NHCOR_5$; Z is halogen, OH, $CF_3$, CN, $COOR_1$, $CONH_2$, $C_1$–$C_4$ alkyl, $C_1$–$C_4$ alkoxy, nitro or $C_1$–$C_4$ dialkylaminomethyl; $R_1$ is hydrogen or $C_1$–$C_4$ alkyl; $R_3$ is $C_1$–$C_5$ alkyl, $C_3$–$C_4$ alkenyl, $C_3$–$C_5$ cycloalkyl, 2-hydroxyethyl, α,α-dimethylphenethyl, benzyl, 3-phenylpropyl or 3-(4-carbomethoxyphenyl)propyl; $R_5$ is hydrogen, $C_1$–$C_4$ alkyl, $C_1$–$C_4$ alkoxy,

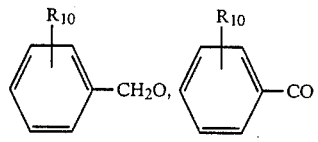

or $N(R_1)_2$; $R_7$ is hydrogen, $C_1$–$C_4$ alkyl or phenyl; $R_8$ is hydrogen, $C_1$–$C_4$ alkyl or $C_3$–$C_4$ alkenyl; $R_9$ is hydrogen, $C_1$–$C_6$ alkyl, $C_4$–$C_6$ cycloalkyl, $C_3$–$C_4$ alkenyl or benzyl; $R_{10}$ is hydrogen, chloro, dichloro, methyl, dimethyl, methoxy, dimethoxy or nitro; and when $R_8$ and $R_9$ are taken together with the nitrogen to which they are attached, they may represent pyrrolidino; with the provisos that when Z is OH, X and Y are hydrogen; when X is —CN, Z is —CN; and when $R_8$ is $C_1$–$C_4$ alkyl or $C_3$–$C_4$ alkenyl, $R_9$ is $C_1$–$C_4$ alkyl or $C_3$–$C_4$ alkenyl; or racemic mixtures of the above-identified compounds, the optically active isomers, or nontoxic, pharmacologically acceptable acid addition salts thereof.

17. An animal feed composition comprising an edible animal feed containing from 0.01 grams to 400 grams of a compound having the structure selected from the group consisting of:

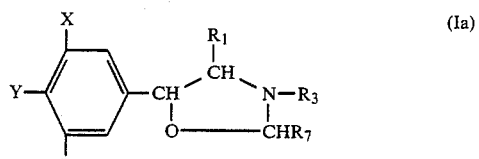
(Ia)

and

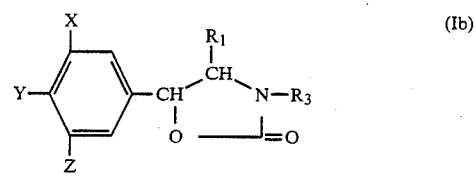
(Ib)

wherein X is hydrogen, halogen, or —CN; Y is hydrogen, $NR_8R_9$ or $NHCOR_5$; Z is halogen, OH, $CF_3$ CN, $COOR_1$, $CONH_2$, $C_1$–$C_4$ alkyl, $C_1$–$C_4$ alkoxy, nitro, or $C_1$–$C_4$ dialkylaminomethyl; $R_1$ is hydrogen or $C_1$–$C_4$ alkyl; $R_3$ is $C_1$–$C_5$ alkyl, $C_3$–$C_4$ alkenyl, $C_3$–$C_5$ cycloalkyl, 2-hydroxyethyl, αα-dimethylphenethyl, benzyl, 3-phenylpropyl or 3-(4-carbomethoxyphenyl)propyl; $R_5$ is hydrogen, $C_1$–$C_4$ alkyl, $C_1$–$C_4$ alkoxy,

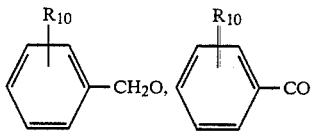

or $N(R_1)_2$; $R_7$ is hydrogen, $C_1$–$C_4$ alkyl or phenyl; $R_8$ is hydrogen, $C_1$–$C_4$ alkyl or $C_3$–$C_4$ alkenyl; $R_9$ is hydrogen, $C_1$–$C_6$ alkyl, $C_4$–$C_6$ cycloalkyl, $C_3$–$C_4$ alkenyl or benzyl; $R_{10}$ is hydrogen, chloro, dichloro, methyl, dimethyl, methoxy, dimethoxy or nitro; and when $R_8$ and $R_9$ are taken together with the nitrogen to which they are attached, they may represent pyrrolidino; with the provisos that when Z is OH, X and Y are hydrogen; when X is —CN, Z is —CN; and when $R_8$ is $C_1$-$C_4$ alkyl, or $C_3$-$C_4$ alkenyl, $R_9$ is $C_1$-$C_4$ alkyl or $C_3$-$C_4$ alkenyl; or racemic mixtures of the above-identified compounds, the optically active isomers, or nontoxic, pharmacologically acceptable acid addition salts thereof.

18. An animal feed supplement comprising about 10% to 25% by weight of a compound having the structure selected from the group consisting of:

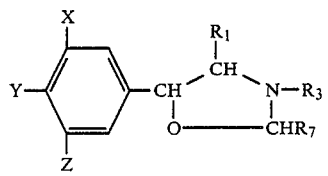
(Ia)

and

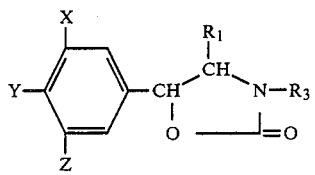
(Ib)

wherein X is hydrogen, halogen, or —CN; Y is hydrogen, $NR_8R_9$ or $NHCOR_5$; Z is halogen, OH, $CF_3$, CN, $COOR_1$, $CONH_2$, $C_1$-$C_4$ alkyl, $C_1$-$C_4$ alkoxy, nitro or $C_1$-$C_4$ dialkylaminomethyl; $R_1$ is hydrogen or $C_1$-$C_4$ alkyl; $R_3$ is $C_1$-$C_5$ alkyl, $C_3$-$C_4$ alkenyl, $C_3$-$C_5$ cycloalkyl, 2-hydroxyethyl, αα-dimethylphenethyl, benzyl, 3-phenylpropyl or 3-(4-carbomethoxyphenyl)propyl; $R_5$ is hydrogen, $C_1$-$C_4$ alkyl, $C_1$-$C_4$ alkoxy,

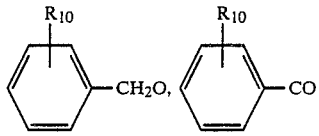

or $N(R_1)_2$; $R_7$ is hydrogen, $C_1$-$C_4$ alkyl or phenyl; $R_8$ is hydrogen, $C_1$-$C_4$ alkyl or $C_3$-$C_4$ alkenyl; $R_9$ is hydrogen, $C_1$-$C_6$ alkyl, $C_4$-$C_6$ cycloalkyl, $C_3$-$C_4$ alkenyl, or benzyl; $R_{10}$ is hydrogen, chloro, dichloro, methyl, dimethyl, methoxy, dimethoxy or nitro; and when $R_8$ and $R_9$ are taken together with the nitrogen to which they are attached, they may represent pyrrolidino; with the provisos that when Y is hydrogen, and X and Z are halogen; when Z is OH, X and Y are hydrogen; when X is —CN, Z is —CN; and when $R_8$ is $C_1$-$C_4$ alkyl or $C_3$-$C_4$ alkenyl, $R_9$ is $C_1$-$C_4$ alkyl or $C_3$-$C_4$ alkenyl; or racemic mixtures of the above-identified compounds, the optically active isomers, or non-toxic, pharmacologically acceptable acid addition salts thereof.

\* \* \* \* \*

UNITED STATES PATENT OFFICE
CERTIFICATE OF CORRECTION

Patent No. 4,522,822  Dated June 11, 1985

Inventor(s) JANE ANNE KIERNAN et al

It is certified that error appears in the above-identified patent and that said Letters Patent are hereby corrected as shown below:

Inventors: should read

Jane Ann Kiernan - Kendal Park,
Pamela Koenig Baker - Hopewell,
both of New Jersey

Signed and Sealed this

Thirtieth Day of December, 1986

*Attest:*

DONALD J. QUIGG

*Attesting Officer*  *Commissioner of Patents and Trademarks*